(12) United States Patent
Yang et al.

(10) Patent No.: US 8,450,437 B2
(45) Date of Patent: May 28, 2013

(54) POLYMERIZATION CATALYSTS FOR PRODUCING POLYMERS WITH LOW MELT ELASTICITY

(75) Inventors: Qing Yang, Bartlesville, OK (US); Max P. McDaniel, Bartlesville, OK (US); Joel L. Martin, Bartlesville, OK (US); Youlu Yu, Bartlesville, OK (US); David C. Rohlfing, Bartlesville, OK (US); Michael D. Jensen, Laurel, MD (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

(21) Appl. No.: 13/349,484

(22) Filed: Jan. 12, 2012

(65) Prior Publication Data

US 2012/0108765 A1 May 3, 2012

Related U.S. Application Data

(62) Division of application No. 11/904,735, filed on Sep. 28, 2007, now Pat. No. 8,119,553.

(51) Int. Cl.
*C08F 4/64* (2006.01)
*C08F 4/76* (2006.01)
*C08F 4/52* (2006.01)

(52) U.S. Cl.
USPC ........... 526/160; 526/170; 526/941; 526/943; 526/127; 526/129; 526/130; 526/135; 526/137; 526/144; 526/348; 526/348.2; 526/348.3; 526/348.4; 526/348.5; 526/348.6; 526/351; 526/352

(58) Field of Classification Search
USPC .......................... 526/160, 170, 348
See application file for complete search history.

(56) References Cited

U.S. PATENT DOCUMENTS

| | | | |
|---|---|---|---|
| 3,242,099 A | 3/1966 | Manyik et al. |
| 3,248,179 A | 4/1966 | Norwood |
| 4,060,480 A | 11/1977 | Reed et al. |
| 4,452,910 A | 6/1984 | Hopkins et al. |
| 4,501,885 A | 2/1985 | Sherk et al. |
| 4,588,790 A | 5/1986 | Jenkins, III et al. |
| 4,794,096 A | 12/1988 | Ewen |

(Continued)

FOREIGN PATENT DOCUMENTS

| | | |
|---|---|---|
| WO | WO 02/38634 | 5/2002 |
| WO | WO 2006/134098 | 12/2006 |

OTHER PUBLICATIONS

Alt, Helmut G., et al., $C_1$-Bridged fluorenylidene cyclopentadienylidene complexes of the type $(C_{13}H_8-CR^1R^2-C_5H_3R)ZrCl_2$ ($R^1$, $R^2$ = alkyl, phenyl, alkenyl; R = H, alkyl, alkenyl, substituted silyl) as catalyst precursors for the polymerization of ethylene and propylene, Journal of Organometallic Chemistry, vol. 568 (1998), pp. 87-112.

(Continued)

*Primary Examiner* — Rip A. Lee
(74) *Attorney, Agent, or Firm* — Fletcher Yoder, PC

(57) ABSTRACT

The present techniques relate to catalyst compositions, methods, and polymers encompassing a Group 4 metallocene compound comprising bridging $\eta^5$-cyclopentadienyl-type ligands, typically in combination with a cocatalyst, and a activator. The compositions and methods presented herein include ethylene polymers with low melt elasticity.

20 Claims, 3 Drawing Sheets

I-1

I-2

I-3

I-4

U.S. PATENT DOCUMENTS

| | | |
|---|---|---|
| 4,808,561 A | 2/1989 | Welborn, Jr. |
| 4,931,417 A | 6/1990 | Miya et al. |
| 4,939,217 A | 7/1990 | Stricklen |
| 5,191,132 A | 3/1993 | Patsidis et al. |
| 5,210,352 A | 5/1993 | Alt et al. |
| 5,347,026 A | 9/1994 | Patsidis et al. |
| 5,352,749 A | 10/1994 | DeChellis et al. |
| 5,369,196 A | 11/1994 | Matsumoto et al. |
| 5,376,611 A | 12/1994 | Shveima |
| 5,385,877 A | 1/1995 | Fujita et al. |
| 5,399,636 A | 3/1995 | Alt et al. |
| 5,401,817 A | 3/1995 | Palackal et al. |
| 5,403,620 A | 4/1995 | Kaesz et al. |
| 5,420,320 A | 5/1995 | Zenk et al. |
| 5,436,304 A | 7/1995 | Griffin et al. |
| 5,436,305 A | 7/1995 | Alt et al. |
| 5,451,649 A | 9/1995 | Zenk et al. |
| 5,455,314 A | 10/1995 | Burns et al. |
| 5,496,781 A | 3/1996 | Geerts et al. |
| 5,498,581 A | 3/1996 | Welch et al. |
| 5,541,272 A | 7/1996 | Schmid et al. |
| 5,545,829 A | 8/1996 | Brekner et al. |
| 5,554,795 A | 9/1996 | Frey et al. |
| 5,563,284 A | 10/1996 | Frey et al. |
| 5,565,175 A | 10/1996 | Hottovy et al. |
| 5,565,592 A | 10/1996 | Patsidis et al. |
| 5,571,880 A | 11/1996 | Alt et al. |
| 5,575,979 A | 11/1996 | Hanson |
| 5,576,259 A | 11/1996 | Hasegawa et al. |
| 5,594,078 A | 1/1997 | Welch et al. |
| 5,627,247 A | 5/1997 | Alt et al. |
| 5,631,203 A | 5/1997 | Welch et al. |
| 5,631,335 A | 5/1997 | Alt et al. |
| 5,654,454 A | 8/1997 | Peifer et al. |
| 5,668,230 A | 9/1997 | Schertl et al. |
| 5,705,578 A | 1/1998 | Peifer et al. |
| 5,705,579 A | 1/1998 | Hawley et al. |
| 5,770,664 A | 6/1998 | Okumura et al. |
| 5,807,938 A | 9/1998 | Kaneko et al. |
| 5,919,983 A | 7/1999 | Rosen et al. |
| 6,107,230 A | 8/2000 | McDaniel et al. |
| 6,114,480 A | 9/2000 | Shamshoum et al. |
| 6,165,929 A | 12/2000 | McDaniel et al. |
| 6,187,880 B1 | 2/2001 | Welch et al. |
| 6,197,902 B1 | 3/2001 | Dolle et al. |
| 6,239,235 B1 | 5/2001 | Hottovy et al. |
| 6,255,417 B1 * | 7/2001 | Oh et al. ............... 526/160 |
| 6,262,191 B1 | 7/2001 | Hottovy et al. |
| 6,294,494 B1 | 9/2001 | McDaniel et al. |
| 6,300,271 B1 | 10/2001 | McDaniel et al. |
| 6,316,553 B1 | 11/2001 | McDaniel et al. |
| 6,316,558 B1 | 11/2001 | Kaneko et al. |
| 6,355,594 B1 | 3/2002 | McDaniel et al. |
| 6,365,764 B1 | 4/2002 | Resconi et al. |
| 6,376,415 B1 | 4/2002 | McDaniel et al. |
| 6,391,816 B1 | 5/2002 | McDaniel et al. |
| 6,395,666 B1 | 5/2002 | McDaniel et al. |
| 6,469,188 B1 | 10/2002 | Miller et al. |
| 6,495,638 B2 | 12/2002 | McDaniel et al. |
| 6,509,427 B1 | 1/2003 | Welch et al. |
| 6,515,086 B1 | 2/2003 | Razavi |
| 6,524,987 B1 | 2/2003 | Collins et al. |
| 6,531,550 B1 | 3/2003 | McDaniel et al. |
| 6,548,441 B1 | 4/2003 | McDaniel et al. |
| 6,548,442 B1 * | 4/2003 | McDaniel et al. ............ 502/113 |
| 6,613,712 B1 | 9/2003 | McDaniel et al. |
| 6,613,852 B2 | 9/2003 | McDaniel et al. |
| 6,632,894 B1 | 10/2003 | McDaniel et al. |
| 6,653,416 B2 | 11/2003 | McDaniel et al. |
| 6,667,274 B1 * | 12/2003 | Hawley et al. ............. 502/415 |
| 6,713,582 B2 * | 3/2004 | DiMaio et al. ............. 526/281 |
| 6,750,302 B1 | 6/2004 | McDaniel et al. |
| 6,831,141 B2 | 12/2004 | McDaniel et al. |
| 6,833,338 B2 | 12/2004 | McDaniel et al. |
| 6,833,415 B2 | 12/2004 | Kendrick et al. |
| 6,858,687 B2 | 2/2005 | McDaniel et al. |
| 6,887,819 B2 | 5/2005 | McDaniel et al. |
| 6,984,603 B2 | 1/2006 | McDaniel et al. |
| 6,992,032 B2 | 1/2006 | McDaniel et al. |
| 7,026,494 B1 | 4/2006 | Yang et al. |
| 7,041,617 B2 * | 5/2006 | Jensen et al. ............... 502/113 |
| 7,064,225 B2 * | 6/2006 | Thorn et al. ............... 556/53 |
| 7,071,276 B2 | 7/2006 | McDaniel et al. |
| 7,094,857 B2 * | 8/2006 | Sukhadia et al. ............. 526/352 |
| 7,148,298 B2 | 12/2006 | Jensen et al. |
| 7,226,886 B2 * | 6/2007 | Jayaratne et al. ............. 502/129 |
| 7,230,128 B2 | 6/2007 | Alt et al. |
| 7,271,124 B2 | 9/2007 | McDaniel et al. |
| 7,312,283 B2 | 12/2007 | Martin et al. |
| 7,470,758 B2 | 12/2008 | Jensen et al. |
| 7,517,939 B2 * | 4/2009 | Yang et al. ............... 526/160 |
| 7,521,572 B2 * | 4/2009 | Jayaratne et al. ............. 556/53 |
| 7,625,982 B2 | 12/2009 | Martin et al. |
| 2005/0113243 A1 | 5/2005 | Thorn et al. |
| 2005/0197470 A1 | 9/2005 | McDaniel et al. |
| 2005/0203261 A1 | 9/2005 | Sukhadia et al. |
| 2005/0288462 A1 | 12/2005 | Jensen et al. |
| 2005/0288524 A1 | 12/2005 | Thorn et al. |
| 2006/0155082 A1 | 7/2006 | McDaniel et al. |
| 2007/0197374 A1 | 8/2007 | Yang et al. |
| 2007/0287814 A1 | 12/2007 | Jensen et al. |
| 2008/0026934 A1 | 1/2008 | Jensen et al. |
| 2008/0108765 A1 | 5/2008 | Busico et al. |
| 2011/0003953 A1 * | 1/2011 | Kirillov et al. ................ 526/170 |

OTHER PUBLICATIONS

Alt, Helmut G., et al., Effect of the Nature of Metallocene Complexes of Group IV Metals of Their Performance in Catalytic Ethylene and Propylene Polymerization, Chem. Rev. 2000, vol. 100, pp. 1205-1221.

Alt, Helmut G., et al., Fluornyl complexes of zirconium and hafnium as catalysts for olefin polymerization, Chemical Society Reviews, 1998, vol. 27, pp. 323-329.

Alt, Helmut G., et al., Syndiospezifische Polymerisation von Propylen: Neue Metallocenkomplexe des Typs ($C_{13}H_{8-n}R_nCR'R''C_5H_4$)$MCl_2$ (n = 0,2; R = Alkyl, Aryl, Hal; R', R''—H, Alkyl, Aryl; M—Zr, Hf) ureter besonderer Berücksichtigung verschiedener Brückensubstituenten, Journal of Organometallic Chemistry, vol. 518 (1996), pp. 7-15.

Alt, Helmut G., et al., Syndiospezifische Polymerisation von Propylen; 2- and 2,7-substituierte Metallocenkomplex des Typs ($C_{13}H_{8-n}R_nCR'_2C_5H_4$)$MCl_2$(n = 1,2; R = Alkoxy, Alkyl, Aryl, Hal; R' = Me, Ph; M = Zr, Hf), Journal of Organometlalic Chemistry, vol. 522, 1996, pp. 39-54.

Köppl, Alexander, et al., Heterogeneous metallocene catalysts for ethylene polymerization, Journal of Molecular Catalysis, A: Chemical 165 (2001), pp. 23-32.

McDaniel, M. P., et al., Ethylene Polymerization Catalysts from Supported Organotransition metal Complexes, III. Support Interactions, Journal of Catalysis, vol. 120, pp. 170-180 (1989).

McDaniel, M. P., Supported Chromium Catalysts for Ethylene Polymerization, Advances in Catalysis, vol. 33, pp. 47-98, (1985).

Salzer, A., Nomenclature of Organometallic Compounds of the Transition Elements, Pure Appl. Chem., vol. 71, No. 8, pp. 1557-1585, 1999, Printed in Great Britain.

Search Report for International Application No. PCT/US2008011055, May 26, 2009.

Search Report for International Application No. PCT/US2008011056, Oct. 1, 2009.

* cited by examiner

R-1

R-2

C-1

POLYMERIZATION CATALYSTS FOR PRODUCING POLYMERS WITH LOW MELT ELASTICITY

CROSS-REFERENCE TO RELATED APPLICATIONS

This application is a divisional of U.S. patent application Ser. No. 11/904,735 now U.S. Pat. No. 8,119,553, entitled "Polymerization Catalysts for Producing Polymers With Low Melt Elasticity" filed on Sep. 28, 2007, which is incorporated by reference herein in its entirety for all purposes.

BACKGROUND OF THE INVENTION

The present techniques relate to the field of organometallic compositions, olefin polymerization catalyst compositions, and methods for the polymerization and copolymerization of olefins using a catalyst composition.

This section is intended to introduce the reader to aspects of art that may be related to aspects of the present techniques, which are described and/or claimed below. Accordingly, it should be understood that these statements are to be read in this light, and not as admissions of prior art.

Polyolefins can be made using catalysts and various types of polymerization reactors that cause the combination of various monomers, such as alpha olefins, into chains of polymer. These alpha olefins are obtained from processing hydrocarbons, such as oil, into various petrochemicals. Different properties may be obtained if two or more different alpha-olefin monomers are polymerized to form a copolymer. If the same alpha-olefin is used for polymerization, the polymer can be referred to as a homopolymer. As these polymer chains are developed during polymerization, they can form solid particles, such as fluff or granules, which possess certain properties and impart various mechanical and physical properties to end products comprising these polymers.

Products made from polyolefins have become increasingly prevalent in society as plastic products. One benefit of these polyolefins is that they are generally non-reactive when put in contact with various goods or products. In particular, plastic products from polyolefin polymers (such as polyethylene, polypropylene, and their copolymers) are used for retail and pharmaceutical packaging (such as display bags, bottles, and medication containers), food and beverage packaging (such as juice and soda bottles), household and industrial containers (such as pails, drums and boxes), household items (such as appliances, furniture, carpeting, and toys), automobile components, fluid, gas and electrical conduction products (such as cable wrap, pipes, and conduits), and various other industrial and consumer products.

Many methods are used for the manufacture of products from polyolefins, including but not limited to, blow-molding, injection-molding, rotational molding, various extrusion methods, thermoforming, sheet molding and casting. The mechanical requirements of the end-product application, such as tensile strength and density, and/or the chemical requirements, such as thermal stability, molecular weight, and chemical reactivity, typically determine what type of polyolefin is suitable and provides the best processing capabilities during manufacture.

BRIEF DESCRIPTION OF THE FIGURES

Advantages of the techniques may become apparent upon reading the following detailed description and upon reference to the drawings in which.

DETAILED DESCRIPTION

Figure 1:
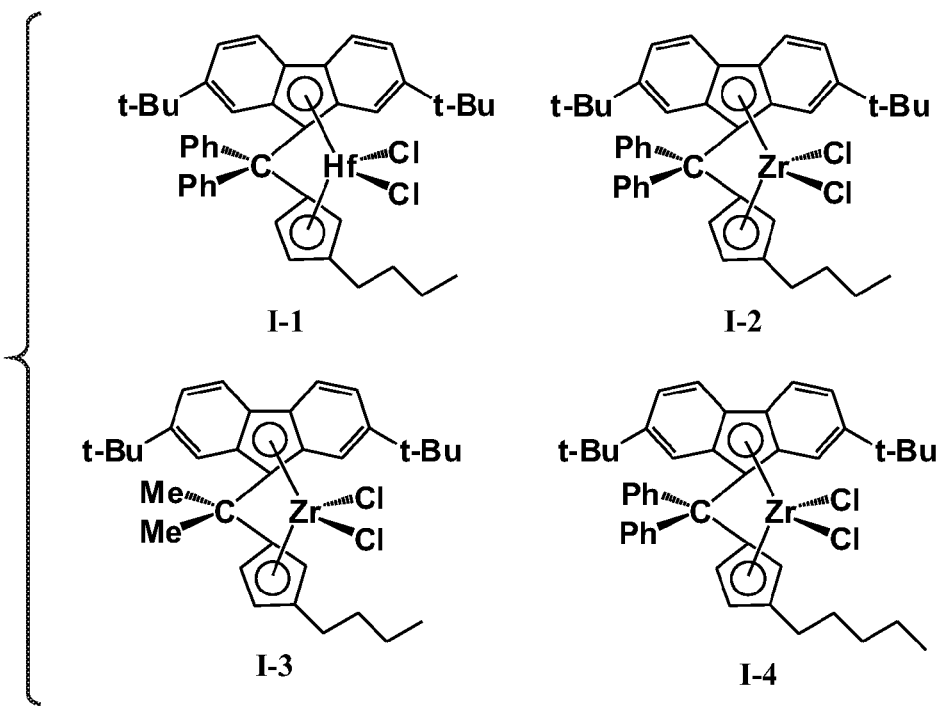
FIG. 1 represents the chemical structures of exemplary metallocenes in accordance with embodiments of the present techniques.

Catalysts that may be used in the polymerization of olefin monomer to polyolefin, e.g., ethylene to polyethylene, include organometallic complexes, such as organic compounds containing metal atoms, such as titanium, zirconium, vanadium, chromium, and so on. During polymerization, these catalysts temporarily attach to the monomer to form an active center that facilitates the sequential addition of monomer units to form the longer polymer chains. The catalysts can be combined with a support or activator-support (e.g., a solid oxide). In addition, the metal catalyst and solid oxide may be blended with a cocatalyst to further activate the catalyst for polymerization. Catalyst compositions of organometallic complexes may be useful both for homopolymerization of ethylene and for copolymerization of ethylene with comonomers such as propylene, 1-butene, 1-hexene, or other higher α-olefins.

Polyethylene (PE) produced by any number of these organometallic catalyst compositions generally has low melt elasticity. Melt elasticity may be considered as the tendency of a molten polymer to flex or distort. While in some circumstances, melt elasticity may be useful, such as for improving bubble stability during the formation of blown film, in some cases melt elasticity causes less than ideal processing capabilities. For example, melt elasticity may be associated with film orientation, melt fracture, and haze. A polymer that has high melt elasticity may develop significant orientation during blown film processing, leading to anisotropic properties. In such a film, the tear strength may be too low in one direction. In other cases, a polymer with high melt elasticity may exhibit severe melt fracturing, in which the polymer has a very irregular or distorted flow during extrusion from a die face, leading to uneven shapes or surface irregularities. In certain cases, the polymer flow may even be interrupted, as the polymer extrudate breaks when it is stretched from the face of the die. Even in less severe cases, melt elasticity may contribute to irregular flow during processing, giving a high surface haze to the finished article.

One of the organometallic complex catalyst systems to be developed in recent years has a metal center attached to a 5-member carbon ring. These systems are called metallocenes. One common type of metallocene system has a bridging group connecting two five membered rings, which are attached to each side of a metal atom to form a sandwich type of structure. These are termed bridging or ansa-metallocenes. While metallocene systems may be more active than other types of catalysts, and ansa-metallocenes may form desirable catalysts for some purposes, they may tend to produce polymer with high melt elasticity which, as discussed above, may not provide the best film performance.

A further challenge in the development of metallocene systems for the polymerization of ethylene is the production of high molecular weight resins. Some metallocene systems may produce resins with lower molecular weights than produced using other types of polyolefin polymerization catalysts. However, the high molecular weight resins produced with some of these other types of polymerization catalysts may display high melt elasticity, which may lead to undesirable film properties in certain product applications. Further, some of these other catalysts may be less efficient at incorporating comonomers. In contrast, tightly bridged metallocenes offer excellent comonomer incorporation, but may still generate resins having too high of a melt elasticity for the desired product application. What is desirable for certain product applications is a catalyst system that will yield high molecular weight resins having low melt elasticity.

Metallocene catalyst systems offer a significant ability to tailor resins by combining multiple metallocene catalysts in a blended system. This ability to tailor resins may be useful in the production of multi-modal resins. For example, the physical properties of such resin blends may be enhanced by higher incorporation of comonomer in the high molecular weight chains versus the lower molecular weight chains. When used in a mixed metallocene catalyst system, the single atom bridged metallocene catalysts of the present techniques may yield high molecular weight resins having low melt elasticity.

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

The present techniques include new catalyst compositions, methods for preparing catalyst compositions, and methods for using the catalyst compositions to polymerize olefins. In some embodiments, the techniques encompass a catalyst composition prepared by contacting a tightly-bridged ansa-metallocene compound including an alkyl group substituent on one of the cyclopentadienyl-type ligands, a support and/or an activator-support, and optionally an organoaluminum compound. The catalyst composition formed as the contact product may include the contacted compounds, reaction products formed from the contacted compounds, or both. In other embodiments, the present techniques include methods for making the catalyst composition presented herein, and in yet other embodiments, the present techniques include methods for polymerizing olefins employing the catalyst composition presented herein. As described above, the designation of the organoaluminum compound as an optional component in the contact product is intended to reflect that the organoaluminum compound may be optional if it is not needed to impart catalytic activity to the catalyst composition, for example, when the metal center already has a single-bonded carbon group as a ligand. To facilitate discussion of the current techniques, the discussion contained herein is presented in sections.

Section I presents catalyst compositions and components in accordance with embodiments of the present techniques. The catalyst compositions and components include exemplary metallocene compounds, optional organoaluminum compounds, activators/cocatalysts, nonlimiting examples of catalyst compositions, and olefin monomers that may be employed in the present techniques.

Section II presents techniques for the preparation of exemplary catalyst compositions using the components discussed in Section I. These preparations include the precontacting of the catalyst compositions with olefins, the use of multiple precontacting steps, the composition ratios that may be used in catalyst compositions of the present techniques, exemplary catalyst preparation processes, and the activities of catalysts (in terms of polymer produced per weight catalyst per hour) that may be obtained from the catalyst compositions of the present techniques.

Section III discusses various processes that the catalyst compositions of the present techniques may be used in for polymerization. Particular processes discussed include loop slurry polymerizations, gas phase polymerizations, and solution phase polymerizations. Other information relevant to the implementation of the catalyst compositions of the current techniques is also presented in this section, including plant systems for feed to and polymer removal from the reactors, particular polymerization conditions, and exemplary products that may be made from polymers formed using the catalyst compositions of the present techniques.

Section IV discloses non-limiting examples of polymers prepared using catalyst compositions in accordance with embodiments of the present techniques. The examples include data indicating the improvements in melt elasticity that may be obtained for polymers made using exemplary catalyst compositions of the present techniques. The results that may be obtained for molecular weights and catalyst activities using the exemplary catalyst compositions are also discussed.

Section V presents experimental procedures that may be used to make and test exemplary catalyst compositions in accordance with embodiments of the present techniques. The techniques include a method that may be used for the determination of relative molecular weight using a standard generated from an absolute determination of molecular weight and a technique for the absolute determination of molecular weight using SEC-MALS. A method for the determination of pore size is discussed. Further, the section includes a discussion of a technique that may be used for the measurement of Tan δ, which was used to determine the melt elasticity. Section V also discusses exemplary techniques for synthesis of the various polymer components. These procedures include techniques for making the fluorided silica-alumina and sulfated alumina activator-supports. The procedures also include techniques for making exemplary metallocenes and polymers, in accordance with embodiments of the present techniques.

I. Catalyst Composition and Components

A. The Metallocene Compounds

1. Overview

The catalyst compositions of the present techniques may include a tightly-bridged ansa-metallocene compound that has an alkyl group of three to 20 carbons bonded to a $\eta^5$-cyclopentadienyl-type ligand (such as, for example, a cyclopentadienyl, an indenyl, or a fluorenyl). The catalyst compositions may also include an activator, and, optionally, an organoaluminum compound as further described below. A general description of the ansa-metallocene complex is presented in the following subsection 2.

The term "bridged" or "ansa-metallocene" refers to a metallocene compound in which the two $\eta^5$-cycloalkadienyl-type ligands in the molecule are linked by a bridging moiety. Useful ansa-metallocenes may be "tightly-bridged," meaning that the two $\eta^5$-cycloalkadienyl-type ligands are connected by a bridging group wherein the shortest link of the bridging moiety between the $\eta^5$-cycloalkadienyl-type ligands is a single atom. The metallocenes described herein are therefore bridged bis($\eta^5$-cycloalkadienyl)-type compounds. The bridging group may have the formula $>ER^1R^2$, wherein E may be a carbon atom, a silicon atom, a germanium atom, or a tin atom, and wherein E is bonded to both $\eta^5$-cyclopentadienyl-type ligands. In this embodiment, $R^1$ and $R^2$ may be independently an alkyl group or an aryl group, either of which having up to 12 carbon atoms, or hydrogen.

The bridging group, $ER^1R^2$, may be: $>CR^1R^2$, $>SiR^1R^2$, $>GeR^1R^2$, or $>SnR^1R^2$, wherein $R^1$ and $R^2$ may be independently an alkyl group or an aryl group, (either of which may have up to 12 carbon atoms), or hydrogen. Such bridging $ER^1R^2$ groups may include, for example, $>CPh_2$, $>SiPh_2$, $>GePh_2$, $>SnPh_2$, $>C(tolyl)_2$, $>Si(tolyl)_2$, $>Ge(tolyl)_2$, $>Sn(tolyl)_2$, $>CMePh$, $>SiMePh$, $>GeMePh$, $>SnMePh$, $>CEtPh$, $>CPrPh$, $>CBuPh$, $>CMe(tolyl)$, $>SiMe(tolyl)$, $>GeMe(tolyl)$, $>SnMe(tolyl)$, $>CHPh$, and $>CH(tolyl)$, among others.

Further, one substituent on the $\eta^5$-cyclopentadienyl-type ligands is a substituted or an unsubstituted alkyl group, which may have up to 12 carbon atoms. The complexes are discussed in the following subsection 3, and shown in the general structural formulas presented therein. Exemplary metallocene complexes, in accordance with embodiments of the present techniques are discussed in the following subsection 4 and shown in FIG. 1.

2. General Metallocene Formula

In embodiments of the present techniques, the ansa-metallocene of the present techniques may be expressed by the general formula:

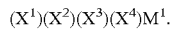

$(X^1)(X^2)(X^3)(X^4)M^1$.

In this formula, $M^1$ may be titanium, zirconium, or hafnium, $X^1$ may be a substituted cyclopentadienyl, a substituted indenyl, or a substituted fluorenyl. $X^2$ may be a substituted cyclopentadienyl or a substituted fluorenyl. One substituent on $X^1$ and $X^2$ is a bridging group having the formula $ER^1R^2$. E may be a carbon atom, a silicon atom, a germanium atom, or a tin atom, and is bonded to both $X^1$ and $X^2$. $R^1$ and $R^2$ may be independently an alkyl group or an aryl group, either of which may have up to 12 carbon atoms, or may be hydrogen. The bridging groups may be selected to influence the activity of the catalyst or the structure of the polymer produced. One substituent on $X^2$ is a substituted or an unsubstituted alkyl group, which may have up to 12 carbon atoms. Substituents $X^3$ and $X^4$ may be independently: 1) F, Cl, Br, or I; 2) a hydrocarbyl group having up to 20 carbon atoms, H, or $BH_4$; 3) a hydrocarbyloxide group, a hydrocarbylamino group, or a trihydrocarbylsilyl group, any of which may have up to 20 carbon atoms; 4) $OBR^4_2$ or $SO_3R^4$, wherein $R^4$ may be an alkyl group or an aryl group, either of which may have up to 12 carbon atoms. Any additional substituent on the substituted cyclopentadienyl, substituted indenyl, substituted fluorenyl, or substituted alkyl group may be independently an aliphatic group, an aromatic group, a cyclic group, a combination of aliphatic and cyclic groups, an oxygen group, a sulfur group, a nitrogen group, a phosphorus group, an arsenic group, a carbon group, a silicon group, or a boron group, any of which may have from 1 to 20 carbon atoms. Alternatively, additional substituents may be present, including halides or hydrogen. The substituents on the if cyclopentadienyl-type ligands may be used to control the activity of the catalyst or the stereochemistry of the polymer produced.

The alkyl group bonded to the $\eta^5$-cyclopentadienyl-type ligands may have up to about 20 carbon atoms, up to about 12 carbon atoms, up to about 8 carbon atoms, or up to about 6 carbon atoms. Such alkyl groups may include, for example, ethyl, propyl, butyl, pentyl, hexyl, heptyl, or octyl, among others.

While an unsubstituted alkyl may be a substituent on the if cyclopentadienyl-type ligands, alternatively, the alkyl group substituent may be further substituted. However, this further substitution may lower the activity of the catalyst. Any substituent present may be selected independently from an aliphatic group, an aromatic group, a cyclic group, a combination of aliphatic and cyclic groups, an oxygen group, a sulfur group, a nitrogen group, a phosphorus group, an arsenic group, a carbon group, a silicon group, a boron group, or a substituted analog thereof, any of which may have from 1 to about 20 carbon atoms. The substituents may also include a halide or hydrogen. Further, this description of other substituents on the alkyl group atom may include substituted, unsubstituted, branched, linear, or heteroatom-substituted analogs of these moieties. Such alkyl groups may include, for example, 3-methyl butyl [$CH_2CH_2CH(CH_3)CH_3$], 4-methylpentyl[$CH_2CH_2CH_2CH(CH_3)_2$, 1,1-dimethylbutyl[$C(CH_3)_2 CH_2CH_2CH_3$], or 1,1-dimethylpentyl[$C(CH_3)_2\ CH_2CH_2 CH_2CH_3$], among others.

In addition to containing a bridging group having the formula $ER^1R^2$ and an alkyl group as described above, the $\eta^5$-cyclopentadienyl-type ligands may also have other substituents. For example, these substituents may be the same chemical groups or moieties that can serve as the $X^3$ or $X^4$ ligands of the ansa-metallocenes. Thus, any additional substituent on the $\eta^5$-cyclopentadienyl-type ligands, the substituted alkyl group, $X^3$, or $X^4$ may be independently such groups as an aliphatic group, an aromatic group, a cyclic group, a combination of aliphatic and cyclic groups, an oxygen group, a sulfur group, a nitrogen group, a phosphorus group, an arsenic group, a carbon group, a silicon group, a boron group, or a substituted analog thereof, any of which having from 1 to about 20 carbon atoms. The substituents may also include a halide or hydrogen, as long as these groups generally do not terminate the activity of the catalyst composition. Further, this list may include substituents that may be characterized in more than one of these categories, such as benzyl. Substituents may also include substituted indenyl and substituted fluorenyl, including partially saturated indenyls and fluorenyls such as, for example, tetrahydroindenyl groups, tetrahydrofluorenyl groups, and octahydrofluorenyl groups. These various substituent groups are further discussed in the paragraphs that follow.

Aliphatic groups that may be used as substituents include, for example, an alkyl group, a cycloalkyl group, an alkenyl group, a cycloalkenyl group, an alkynyl group, an alkadienyl group, a cyclic group, and the like. This may include all substituted, unsubstituted, branched, and linear analogs or derivatives thereof, wherein each group may have from one to about 20 carbon atoms. Thus, aliphatic groups may include, for example, hydrocarbyls such as paraffins and alkenyls. For example, the aliphatic groups may include such groups as methyl, ethyl, propyl, n-butyl, tert-butyl, sec-butyl, isobutyl, amyl, isoamyl, hexyl, cyclohexyl, heptyl, octyl, nonyl, decyl, dodecyl, 2-ethylhexyl, pentenyl, butenyl, and the like.

Aromatic groups that may be used as substituents include, for example, phenyl, naphthyl, anthracenyl, and the like. Substituted derivatives of these compounds are also included, wherein each group may have from 6 to about 25 carbons. Such substituted derivatives may include, for example, tolyl, xylyl, mesityl, and the like, including heteroatom substituted derivatives thereof.

Cyclic groups that may be used as substituents include, for example, cycloparaffins, cycloolefins, cycloacetylenes, arenes such as phenyl, bicyclic groups and the like, as well as substituted derivatives thereof, in each occurrence having from about 3 to about 20 carbon atoms. Thus, heteroatom-substituted cyclic groups such as furanyl may be included herein. Such substituents may include, aliphatic and cyclic groups, e.g., groups that have both an aliphatic portion and a cyclic portion. Examples of these substituents may include groups such as: —$(CH_2)_mC_6H_qR_{5-q}$ wherein m may be an integer from 1 to about 10, and q may be an integer from 1 to 5, inclusive; —$(CH_2)_mC_6H_qR_{11-q}$ wherein m may be an integer from 1 to about 10, and q may be an integer from 1 to 11, inclusive; or —$(CH_2)_mC_5H_qR_{9-q}$ wherein m may be an integer from 1 to about 10, and q may be an integer from 1 to 9, inclusive. As defined above, R may be independently selected from: an aliphatic group; an aromatic group; a cyclic group; any combination thereof; any substituted derivative thereof, including, but not limited to, a halide-, an alkoxide-, or an amide-substituted derivative or analog thereof; any of which has from 1 to about 20 carbon atoms; or hydrogen. In various embodiments, such aliphatic and cyclic groups may include, for example: —$CH_2C_6H_5$; —$CH_2C_6H_4F$; —$CH_2C_6H_4Cl$; —$CH_2C_6H_4Br$; —$CH_2C_6H_4I$; —$CH_2C_6H_4OMe$; —$CH_2C_6H_4OEt$; —$CH_2C_6H_4NH_2$; —$CH_2C_6H_4NMe_2$; —$CH_2C_6H_4NEt_2$; —$CH_2CH_2C_6H_5$; —$CH_2CH_2C_6H_4F$; —$CH_2CH_2C_6H_4Cl$; —$CH_2CH_2C_6H_4Br$; —$CH_2CH_2C_6H_4I$; —$CH_2CH_2C_6H_4OMe$; —$CH_2CH_2C_6H_4OEt$; —$CH_2CH_2C_6H_4NH_2$; —$CH_2CH_2C_6H_4NMe_2$; —$CH_2CH_2C_6H_4NEt_2$; any regioisomer thereof, and any substituted derivative thereof.

Substituents may contain heteroatoms, including, for example, halides, oxygen, sulfur, nitrogen, phosphorous, or arsenic. Examples of halides include fluoride, chloride, bromide, and iodide. As used herein, oxygen groups are oxygen-containing groups, including, for example, alkoxy or aryloxy groups (—OR) and the like, wherein R may be alkyl, cycloalkyl, aryl, aralkyl, substituted alkyl, substituted aryl, or substituted aralkyl having from 1 to about 20 carbon atoms. Such alkoxy or aryloxy groups (—OR) groups may include, for example, methoxy, ethoxy, propoxy, butoxy, phenoxy, or substituted phenoxy, among others. As used herein, sulfur groups are sulfur-containing groups, including, for example, —SR and the like, wherein R may be alkyl, cycloalkyl, aryl, aralkyl, substituted alkyl, substituted aryl, or substituted aralkyl having from 1 to about 20 carbon atoms. As used herein, nitrogen groups are nitrogen-containing groups, which may include, for example, —$NR_2$ or pyridyl groups, and the like, wherein R may be alkyl, cycloalkyl, aryl, aralkyl, substituted alkyl, substituted aryl, or substituted aralkyl having from 1 to about 20 carbon atoms. As used herein, phosphorus groups are phosphorus-containing groups, which may include, for example, —$PR_2$, and the like, wherein R may be alkyl, cycloalkyl, aryl, aralkyl, substituted alkyl, substituted aryl, or substituted aralkyl having from 1 to about 20 carbon atoms. As used herein, arsenic groups are arsenic-containing groups, which may include, for example, —$AsR_2$, and the like, wherein R may be alkyl, cycloalkyl, aryl, aralkyl, substituted alkyl, substituted aryl, or substituted aralkyl having from 1 to about 20 carbon atoms.

As used herein, carbon groups are carbon-containing groups, which may include, for example, alkyl halide groups. Such alkyhalide groups may include halide-substituted alkyl groups with 1 to about 20 carbon atoms, alkenyl or alkenyl halide groups with 1 to about 20 carbon atoms, aralkyl or aralkyl halide groups with 1 to about 20 carbon atoms, and the like, including substituted derivatives thereof.

As used herein, silicon groups are silicon-containing groups, which may include, for example, silyl groups such alkylsilyl groups, arylsilyl groups, arylalkylsilyl groups, siloxy groups, and the like, having from 1 to about 20 carbon atoms. For example, silicon groups include trimethylsilyl and phenyloctylsilyl groups.

As used herein, boron groups are boron-containing groups, which may include, for example, —$BR_2$, —$BX_2$, —BRX, wherein X may be a monoanionic group such as halide, hydride, alkoxide, alkyl thiolate, and the R may be alkyl, cycloalkyl, aryl, aralkyl, substituted alkyl, substituted aryl, or substituted aralkyl having from 1 to about 20 carbon atoms.

The remaining substituents on the metal center, $X^3$ and $X^4$, may be independently an aliphatic group, a cyclic group, a combination of an aliphatic group and a cyclic group, an amido group, a phosphido group, an alkyloxide group, an aryloxide group, an alkanesulfonate, an arenesulfonate, or a trialkylsilyl, or a substituted derivative thereof, any of which having from 1 to about 20 carbon atoms; or a halide. More specifically, $X^3$ and $X^4$ may be independently: 1) F, Cl, Br, or I; 2) a hydrocarbyl group having up to 20 carbon atoms, H, or $BH_4$; 3) a hydrocarbyloxide group, a hydrocarbylamino group, or a trihydrocarbylsilyl group, any of which having up to 20 carbon atoms; 4) $OBR^A_2$ or $SO_3R^A$, wherein $R^A$ may be an alkyl group or an aryl group, any of which having up to 12 carbon atoms.

3. General Structural Formulas for Metallocene Catalysts

Embodiments of the current techniques may include an ansa-metallocene having the general formula:

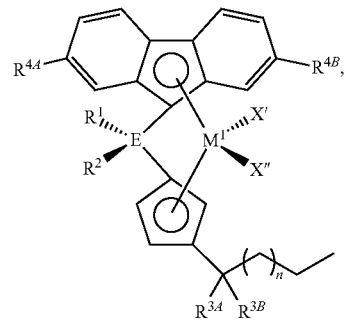

wherein $M^1$ may be zirconium or hafnium and X' and X" may be independently F, Cl, Br, or I. E may be C or Si and $R^1$ and $R^2$ may be independently an alkyl group or an aryl group, either of which may have up to 10 carbon atoms, or $R^1$ and $R^2$ may be hydrogen. $R^{3A}$ and $R^{3B}$ may be independently a hydrocarbyl group or a trihydrocarbylsilyl group, any of which may have up to 20 carbon atoms, or may be hydrogen. The subscript 'n' may be an integer that may range from 0 to 10, inclusive. $R^{4A}$ and $R^{4B}$ may be independently a hydrocarbyl group that may have up to 12 carbon atoms, or may be hydrogen.

In other embodiments, the ansa-metallocene may include a compound having the formula:

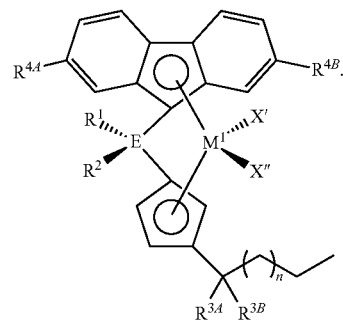

In this formula, $M^1$ may be zirconium or hafnium, and X' and X" may be independently F, Cl, Br, or I. E may be C or Si and $R^1$ and $R^2$ may be independently an alkyl group or an aryl group, either of which having up to 10 carbon atoms, or hydrogen. $R^{3A}$ and $R^{3B}$ may be independently H, methyl, allyl, benzyl, butyl, pentyl, hexyl, or trimethylsilyl, and 'n' may be an integer from 1 to 6, inclusive. $R^{4A}$ and $R^{4B}$ may be independently a hydrocarbyl group having up to 6 carbon atoms, or hydrogen.

In still other embodiments, the ansa-metallocene may include a compound having the formula:

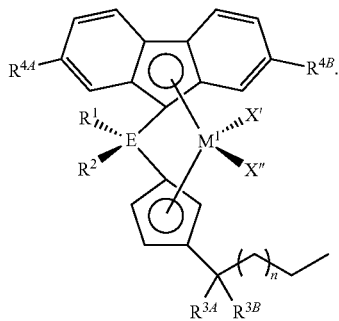

In this formula, $M^1$ may be zirconium or hafnium, and X' and X" may be independently F, Cl, Br, or I. E may be C or Si and $R^1$ and $R^2$ may be independently methyl or phenyl. $R^{3A}$ and $R^{3B}$ may be independently H or methyl, and n may be 1 or 2. $R^{4A}$ and $R^{4B}$ may be independently H or t-butyl.

In yet other embodiments, the ansa-metallocene of the present techniques may include a compound having the formula:

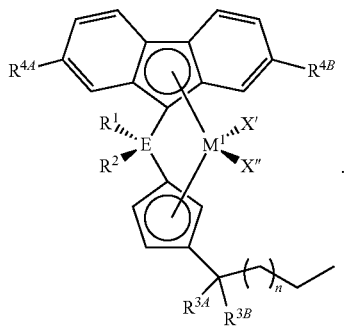

In this formula, $M^1$ may be zirconium or hafnium, and X' and X" may be independently H, $BH_4$, methyl, phenyl, benzyl, neopentyl, trimethylsilylmethyl, $CH_2CMe_2Ph$; $CH_2SiMe_2Ph$; $CH_2CMe_2CH_2Ph$; or $CH_2SiMe_2CH_2Ph$. E may be C or Si and $R^1$ and $R^2$ may be independently an alkyl group or an aryl group, either of which having up to 10 carbon atoms, or hydrogen. $R^{3A}$ and $R^{3B}$ may be independently a hydrocarbyl group or a trihydrocarbylsilyl group, any of which having up to 20 carbon atoms, or hydrogen, and n may be an integer from 0 to 10, inclusive. $R^{4A}$ and $R^{4B}$ may be independently a hydrocarbyl group having up to 12 carbon atoms, or hydrogen.

4. Non-limiting Examples of Metallocene Structures

In exemplary embodiments, the ansa-metallocene may include any of compounds (I-1) through (I-4), as shown in FIG. 1, or any combination thereof. Numerous processes to prepare metallocene compounds that may be employed in the present techniques have been reported. For example, U.S. Pat. Nos. 4,939,217, 5,191,132, 5,210,352, 5,347,026, 5,399,636, 5,401,817, 5,420,320, 5,436,305, 5,451,649, 5,496,781, 5,498,581, 5,541,272, 5,554,795, 5,563,284, 5,565,592, 5,571,880, 5,594,078, 5,631,203, 5,631,335, 5,654,454, 5,668,230, 5,705,578, 5,705,579, 6,187,880, and 6,509,427 describe such methods, each of which is incorporated by reference in its entirety herein.

B. Optional Organoaluminum Compounds

In one embodiment, the present techniques may include a catalyst composition including a tightly-bridged ansa-metallocene compound having an alkyl moiety bonded to a $\eta^5$-cyclopentadienyl-type ligand, a solid oxide activator-support, and, optionally, an organoaluminum compound. The designation of the organoaluminum compound as "optional" is intended to reflect that the organoaluminum compound may be optional when it may not be needed to impart catalytic activity to the catalyst composition.

Organoaluminum compounds that may be used in the present techniques include, for example, compounds with the formula:

$$Al(X^5)_n(X^6)_{3-n},$$

wherein $X^5$ may be a hydrocarbyl having from 1 to about 20 carbon atoms; $X^6$ may be alkoxide or aryloxide, any of which having from 1 to about 20 carbon atoms, halide, or hydride; and n may be a number from 1 to 3, inclusive. In various embodiments, $X^5$ may be an alkyl having from 1 to about 10 carbon atoms. Moieties used for $X^5$ may include, for example, methyl, ethyl, propyl, butyl, sec-butyl, isobutyl, 1-hexyl, 2-hexyl, 3-hexyl, isohexyl, heptyl, or octyl, and the like. In other embodiments, $X^6$ may be independently fluoride, chloride, bromide, methoxide, ethoxide, or hydride. In yet another embodiment, $X^6$ may be chloride.

In the formula $Al(X^5)_n(X^6)_{3-n}$, may be a number from 1 to 3 inclusive, and in an exemplary embodiment, n is 3. The value of n is not restricted to an integer, therefore this formula may include sesquihalide compounds, other organoaluminum cluster compounds, and the like.

Generally, organoaluminum compounds that may be used in the present techniques may include trialkylaluminum compounds, dialkylaluminium halide compounds, dialkylaluminum alkoxide compounds, dialkylaluminum hydride compounds, and combinations thereof. Examples of such organoaluminum compounds include trimethylaluminum, triethylaluminum (TEA), tripropylaluminum, tributylaluminum, tri-n-butylaluminum (TNBA), triisobutylaluminum (TIBA), trihexylaluminum, triisohexylaluminum, trioctylaluminum, diethylaluminum ethoxide, diisobutylaluminum hydride, or diethylaluminum chloride, or any combination thereof. If the particular alkyl isomer is not specified, the compound may encompass all isomers that can arise from a particular specified alkyl group.

In some embodiments, the present techniques may include precontacting the ansa-metallocene with an organoaluminum compound and an olefin monomer to form a precontacted mixture, prior to contacting this precontacted mixture with the solid oxide activator-support to form the active catalyst. When the catalyst composition is prepared in this manner, a portion of the organoaluminum compound may be added to the precontacted mixture and another portion of the organoaluminum compound may be added to the postcontacted mixture prepared when the precontacted mixture is contacted with the solid oxide activator. However, all of the organoaluminum compound may be employed to prepare the catalyst in either the precontacting or postcontacting step. Alternatively, the solid oxide may also be treated with aluminum alkyl before being treated with metallocene or other mixtures. These precontacting steps are not required, and all of the catalyst components may be contacted in a single step.

Further, more than one organoaluminum compound may be used, in either the precontacting or the postcontacting step, or in any procedure in which the catalyst components are contacted. When an organoaluminum compound is added in multiple steps, the amounts of organoaluminum compound presented herein include the total amount of organoaluminum compound used in both the precontacted and postcontacted mixtures, and any additional organoaluminum compound added to the polymerization reactor. Therefore, total amounts of organoaluminum compounds are presented, regardless of whether a single organoaluminum compound is used, or more than one organoaluminum compound. Again, exemplary organoaluminum compounds used in embodiments of the present techniques may include, for example, triethylaluminum (TEA), tri-n-butylaluminum (TNBA), triisobutylaluminum (TIBA), and so on, or any combination thereof.

C. The Activator/Cocatalyst

1. Overview

Embodiments of the present techniques encompass a catalyst composition including: a tightly-bridged ansa-metallocene compound as presented herein, optionally, an organoaluminum compound, and an activator. The activator may be required to weaken the bonds between the metal center and ligands $X^3$ or $X^4$, discussed above, allowing complexation of the metal center with an olefin. Further, an activator or co-catalyst may replace $X^3$ or $X^4$ with a carbon group having a single-bond to the metal. The activator may be an activator-support including: a solid oxide treated with an electron-withdrawing anion, as discussed in the following subsection 2; an ion-exchangeable or layered mineral activator-support, as discussed in the following subsection 3; an organoaluminoxane compound, as discussed in the following subsection 4; an organoboron or organoborate compound, as discussed in the following subsection 5; or an ionizing compound, as discussed in the following subsection 6; or any combination of any of these activators.

In some embodiments, aluminoxane may not be required to form the catalyst composition as presented herein, a feature that allows lower polymer production costs. Accordingly, $AlR_3$-type organoaluminum compounds and one or more activator-supports may be used in the absence of aluminoxanes. While not intending to be bound by theory, it is believed that the organoaluminum compounds may not activate the metallocene catalysts in the same manner as an organoaluminoxane.

Additionally, no borate compounds or $MgCl_2$ may be required to form the catalyst composition of the present techniques, although aluminoxane, borate compounds, $MgCl_2$, or any combination thereof, may optionally be used in the catalyst composition of the present techniques. Further, in such compounds as aluminoxanes, organoboron compounds, ionizing ionic compounds, or any combination thereof, may be used as cocatalysts with the ansa-metallocene, either in the presence or absence of the activator support. Such cocatalysts may be used with the ansa-metallocene, either in the presence or absence of an organoaluminum compound, as specified herein. Thus, the organoaluminum compound is optional: when a ligand on the metallocene is a hydrocarbyl group, H, or $BH_4$; when the activator includes an organoaluminoxane compound; or when both these conditions are present. However, the catalyst compositions of the present techniques may be active in the substantial absence of cocatalysts such as aluminoxanes, organoboron compounds, ionizing ionic compounds, or any combination thereof.

2. Chemically-Treated Solid Oxide Activator-Supports a. Overview

The present techniques encompass catalyst compositions that include an acidic activator-support, such as, for example, a chemically-treated solid oxide (CTSO). A CTSO may be used in combination with an organoaluminum compound. The activator-support may include a solid oxide treated with an electron-withdrawing anion. The solid oxide may include such compounds as silica, alumina, silica-alumina, aluminophosphate, aluminum phosphate, zinc aluminate, heteropolytungstates, titania, zirconia, magnesia, boria, zinc oxide, mixed oxides thereof, and the like, or any mixture or combination thereof. The electron-withdrawing anion may include fluoride, chloride, bromide, iodide, phosphate, triflate, bisulfate, sulfate, sulfite, fluoroborate, fluorosulfate, trifluoroacetate, phosphate, fluorophosphate, fluorozirconate, fluorosilicate, fluorotitanate, permanganate, substituted or unsubstituted alkanesulfonate, substituted or unsubstituted arenesulfonate, substituted or unsubstituted alkylsulfate, or any combination thereof.

The activator-support may include the contact product of a solid oxide compound and an electron-withdrawing anion source, as presented in the following subsection b. The solid oxide compound may include an inorganic oxide and may be optionally calcined prior to contacting the electron-withdrawing anion source. The contact product may also be calcined either during or after the solid oxide compound is contacted with the electron-withdrawing anion source. In this embodiment, the solid oxide compound may be calcined or uncalcined. In another embodiment, the activator-support may include the contact product of a calcined solid oxide compound and an electron-withdrawing anion source.

The treated activator-support may exhibit enhanced activity as compared to the corresponding untreated solid oxide compound. While not intending to be bound by theory, it is believed that the activator-support can function as a solid oxide supporting compound with an additional ionizing, polarizing, or bond weakening function, collectively termed an "activating" function, by weakening the metal-ligand bond between an anionic ligand and the metal in the metallocene. Thus, the activator-support may be considered to exhibit an "activating" function, regardless of whether it ionizes the metallocene, abstracts an anionic ligand to form an ion pair, weakens the metal-ligand bond in the metallocene, simply coordinates to an anionic ligand when it contacts the activator-support, or any other mechanisms by which ionizing, polarizing, or bond weakening might occur. In preparing the metallocene-based catalyst compositions of the present techniques, the activator-support is typically used along with a component that provides an activatable ligand such as an alkyl or hydride ligand to the metallocene, including but not limited to an organoaluminum compound, when the metallocene compound does not already include such a ligand. In one embodiment the treated solid oxide may be contacted with the aluminum alkyl before being exposed to the metallocene.

The activator-support may include a solid inorganic oxide material, a mixed oxide material, or a combination of inorganic oxide materials that is chemically-treated with an electron-withdrawing component, and optionally treated with another metal ion. Thus, the solid oxide of the present techniques encompasses oxide materials such as alumina, "mixed oxide" compounds such as silica-alumina or silica-zirconia or silica-titania, and combinations and mixtures thereof. The mixed metal oxide compounds such as silica-alumina, with more than one metal combined with oxygen to form a solid oxide compound, may be made by co-gellation, impregnation or chemical deposition, and are encompassed by the present techniques.

Further, the activator-support may include an additional metal or metal ion such as zinc, nickel, vanadium, silver, copper, gallium, tin, tungsten, molybdenum, or any combination thereof. Examples of activator-supports that further include an additional metal or metal ion include, for example, chlorided zinc-impregnated alumina, fluorided zinc-impregnated alumina, chlorided vanadium-impregnated alumina, fluorided zinc-impregnated silica-alumina, chlorided nickel-impregnated alumina, or any combination thereof.

The activator-support of the present techniques may include a solid oxide of relatively high porosity, which exhibits Lewis acidic or Brønsted acidic behavior. The solid oxide may be chemically-treated with an electron-withdrawing component, typically an electron-withdrawing anion, to form an activator-support. While not intending to be bound by theory, it is believed that treatment of the inorganic oxide with an electron-withdrawing component augments or enhances the acidity of the oxide. Thus, the activator-support exhibits Lewis or Brønsted acidity which is typically greater than the Lewis or Brønsted acidity of the untreated solid oxide. The polymerization activity of the chemically-treated solid oxide may be enhanced over the activity shown by an untreated solid oxide.

The chemically-treated solid oxide may include a solid inorganic oxide, including oxygen and an element selected from Group 2, 3, 4, 5, 6, 7, 8, 9, 10, 11, 12, 13, 14, or 15 of the periodic table, or including oxygen and an element selected from the lanthanide or actinide elements. For example, the inorganic oxide may include oxygen and an element selected from Al, B, Be, Bi, Cd, Co, Cr, Cu, Fe, Ga, La, Mn, Mo, Ni, Sb, Si, Sn, Sr, Th, Ti, V, W, P, Y, Zn or Zr.

Suitable solid oxide materials or compounds that may be used in the chemically-treated solid oxide of the present techniques may include, for example, $Al_2O_3$, $B_2O_3$, $BeO$, $Bi_2O_3$, $CdO$, $CO_3O_4$, $Cr_2O_3$, $CuO$, $Fe_2O_3$, $Ga_2O_3$, $La_2O_3$, $Mn_2O_3$, $MoO_3$, $NiO$, $P_2O_5$, $Sb_2O_5$, $SiO_2$, $SnO_2$, $SrO$, $ThO_2$, $TiO_2$, $V_2O_5$, $WO_3$, $Y_2O_3$, $ZnO$, $ZrO_2$, and the like, including mixed oxides thereof, and combinations thereof. Mixed oxides that may be used in the activator-support of the present techniques may include, for example, mixed oxides of any combination of Al, B, Be, Bi, Cd, Co, Cr, Cu, Fe, Ga, La, Mn, Mo, Ni, P, Sb, Si, Sn, Sr, Th, Ti, V, W, Y, Zn, Zr, and the like. Examples of mixed oxides that may be used in the activator-support of the present techniques may also include silica-alumina, silica-titania, silica-zirconia, zeolites, many clay minerals, pillared clays, alumina-titania, alumina-zirconia, aluminophosphate, and the like. Procedures to form such solid oxides, and exemplary chemically treated solid oxides are presented in the following subsections c and d, respectively. Concentrations of electron-withdrawing anions that may be useful in forming chemically treated solid oxides are presented in the following subsection e.

b. Chemical Treatment of the Solid Oxide

A solid oxide material that may be used in the present techniques may be chemically-treated by contacting it with an electron-withdrawing component, typically an electron-withdrawing anion source, to cause or enhance activation of the metallocene complex. Further, the solid oxide material may be chemically-treated with another metal ion, that may be the same as or different from any metal element that constitutes the solid oxide material, then calcined to form a metal-containing or metal-impregnated chemically-treated solid oxide. Alternatively, a solid oxide material and an electron-withdrawing anion source may be contacted and calcined simultaneously. The method by which the oxide may be contacted with an electron-withdrawing component, typically a salt or an acid of an electron-withdrawing anion, may include, for example, gelling, co-gelling, impregnation of one compound onto another, vaporization of one compound onto the other, and the like. In embodiments of the present techniques, following any contacting method, the contacted mixture of oxide compound, electron-withdrawing anion, and optionally the metal ion may be calcined.

The electron-withdrawing component used to treat the oxide may be any component that increases the Lewis or Brønsted acidity of the solid oxide upon treatment. In one embodiment, the electron-withdrawing component is typically an electron-withdrawing anion derived from a salt, an acid, or other compound such as a volatile organic compound that can serve as a source or precursor for that anion. Examples of electron-withdrawing anions include, for example, fluoride, chloride, bromide, iodide, phosphate, trifluoromethane sulfonate (triflate), bisulfate, sulfate, fluoroborate, fluorosulfate, trifluoroacetate, phosphate, fluorophosphate, fluorozirconate, fluorosilicate, fluorotitanate, permanganate, substituted or unsubstituted alkanesulfonate, substituted or unsubstituted arenesulfonate, substituted or unsubstituted alkylsulfate, and the like, including any mixtures and combinations thereof. In addition, other ionic or non-ionic compounds that serve as sources for these electron-withdrawing anions may also be used in the present techniques. The chemically-treated solid oxide may include a sulfated solid oxide or a sulfated alumina.

The terms alkanesulfonate and alkyl sulfate refer to anions having the general formula $[R^B SO_2 O]^-$ and $[(R^B O)SO_2 O]^-$, respectively, wherein $R^B$ may be a linear or branched alkyl group having up to 20 carbon atoms, that may be substituted with a group selected independently from F, Cl, Br, I, OH, OMe, OEt, $OCF_3$, Ph, xylyl, mesityl, or OPh. Thus, the alkanesulfonate and alkyl sulfate may be referred to as being either substituted or unsubstituted. In one embodiment, the alkyl group of the alkanesulfonate or alkyl sulfate may have up to 12 carbon atoms. In another embodiment, the alkyl group of the alkanesulfonate or alkyl sulfate may have up to 8 carbon atoms, or up to 6 carbon atoms. Such alkanesulfonates may include, for example, methanesulfonate, ethanesulfonate, 1-propanesulfonate, 2-propanesulfonate, 3-methylbutanesulfonate, trifluoromethanesulfonate, trichloromethanesulfonate, chloromethanesulfonate, 1-hydroxyethanesulfonate, 2-hydroxy-2-propanesulfonate, 1-methoxy-2-propanesulfonate, and the like. In other embodiments, examples of alkyl sulfates include, for example, methylsulfate, ethylsulfate, 1-propylsulfate, 2-propylsulfate, 3-methylbutylsulfate, trifluoromethanesulfate, trichloromethylsulfate, chloromethylsulfate, 1-hydroxyethylsulfate, 2-hydroxy-2-propylsulfate, 1-methoxy-2-propylsulfate, and the like.

The term arenesulfonate refers to anions having the general formula $[Ar^4 SO_2 O]^-$, wherein $Ar^4$ may be an aryl group having up to 14 carbon atoms, and which may be optionally substituted with a group selected independently from F, Cl, Br, I, Me, Et, Pr, Bu, OH, OMe, OEt, OPr, OBu, $OCF_3$, Ph, OPh, or $R^C$, wherein $R^C$ may be a linear or branched alkyl group having up to 20 carbon atoms. Thus, the arenesulfonate may be referred to as a substituted or an unsubstituted arenesulfonate. Because the aryl group $Ar^4$ may be substituted with an alkyl side chain, $R^C$, which may include a long alkyl side chain, the term arenesulfonate encompasses detergents. The aryl group of the arenesulfonate may have up to 10 carbon atoms, or up to 6 carbon atoms. Examples of such arenesulfonates include, for example, benzenesulfonate, naphthalenesulfonate, p-toluenesulfonate, m-toluenesulfonate, 3,5-xylenesulfonate, trifluoromethoxybenzenesulfonate, trichloromethoxybenzenesulfonate, trifluoromethyl-benzenesulfonate, trichloromethylbenzenesulfonate, fluorobenzenesulfonate, chlorobenzenesulfonate, 1-hydroxyethanebenzenesulfonate, 3-fluoro-4-methoxybenzenesulfonate, and the like.

When the electron-withdrawing component includes a salt of an electron-withdrawing anion, the counterion or cation of that salt may be any cation that allows the salt to revert or decompose back to the acid during calcining Factors that dictate the suitability of the particular salt to serve as a source for the electron-withdrawing anion may include, for example, the solubility of the salt in the desired solvent, the lack of adverse reactivity of the cation, ion-pairing effects between the cation and anion, hygroscopic properties imparted to the salt by the cation, and the like, and thermal stability of the anion. Examples of suitable cations in the salt of the electron-withdrawing anion include, for example, ammonium, trialkyl ammonium, tetraalkyl ammonium, tetraalkyl phosphonium, $H^+$, $[H(OEt_2)_2]^+$, and the like.

c. Examples of Processes to Produce a Chemically Treated Solid Oxide

Combinations of one or more different electron withdrawing anions, in varying proportions, may be used to tailor the specific acidity of the activator-support to the desired level. Such combinations may be contacted with the oxide material simultaneously or individually, and in any order that affords the desired activator-support acidity. For example, the present techniques may employ two or more electron-withdrawing anion source compounds in two or more separate contacting steps. Thus, one example of such a process by which an activator-support may be prepared is as follows. A selected solid oxide compound, or combination of oxide compounds, is contacted with a first electron-withdrawing anion source compound to form a first mixture and this first mixture is calcined. The calcined first mixture is contacted with a second electron-withdrawing anion source compound to form a second mixture. The second mixture is calcined to form a treated solid oxide compound. In such a process, the first and second electron-withdrawing anion source compounds may be different compounds or they may be the same compound.

The solid oxide activator-support may be produced by a process that includes contacting a solid oxide compound with an electron-withdrawing anion source compound to form a first mixture. The first mixture is then calcined to form the solid oxide activator-support.

In other embodiments, the solid oxide activator-support may be produced by a process that includes contacting a solid oxide compound with a first electron-withdrawing anion source compound to form a first mixture. The first mixture is calcined, and then the calcined first mixture is contacted with a second electron-withdrawing anion source compound to form a second mixture. The second mixture is calcined to form the solid oxide activator-support. The solid oxide activator-support may be referred to as a chemically treated solid oxide (CTSO) compound.

Alternatively, the solid oxide activator-support may be produced by contacting a solid oxide with an electron-withdrawing anion source compound. In this procedure the solid oxide compound may be calcined before, during or after contacting with the electron-withdrawing anion source, and when there are aluminoxanes or organoborates present.

Calcining of the treated solid oxides may be conducted in an ambient or inert atmosphere, typically in a dry ambient atmosphere, at a temperature from about 200° C. to about 900° C., and for a time of about 1 minute to about 100 hours. In other embodiments, calcining may be conducted at a temperature from about 300° C. to about 800° C. and in yet other embodiments, calcining may be conducted at a temperature from about 400° C. to about 700° C. Calcining may be conducted from about 1 hour to about 50 hours, or from about 3 hours to about 20 hours. In exemplary embodiments, calcining may be carried out from about 1 to about 10 hours at a temperature from about 350° C. to about 550° C.

Further, calcining may typically be conducted in an ambient atmosphere, at the elevated temperature. Generally, calcining may be conducted in an oxidizing atmosphere, such as air. Alternatively, calcining may be performed in an inert atmosphere, such as nitrogen or argon, or in a reducing atmosphere such as hydrogen or carbon monoxide.

The solid oxide component used to prepare the chemically-treated solid oxide may have a pore volume greater than about 0.1 cc/g, a pore volume greater than about 0.5 cc/g, or a pore volume greater than about 1.0 cc/g. The solid oxide component may have a surface area from about 100 to about 1000 $m^2/g$, from about 200 to about 800 $m^2/g$, or from about 250 to about 600 $m^2/g$.

d. Examples of Chemically Treated Solid Oxides

The solid oxide material may be treated with a source of halide ion or sulfate ion, or a combination of anions, and optionally treated with a metal ion, then calcined to provide the activator-support in the form of a particulate solid. For example, the solid oxide material may be treated with a source of sulfate, termed a sulfating agent, a source of chloride ion, termed a chloriding agent, a source of fluoride ion, termed a fluoriding agent, or a combination thereof, and calcined to provide the solid oxide activator. Examples of useful acidic activator-supports may include, for example: bromided alumina; chlorided alumina; fluorided alumina; sulfated alumina; bromided silica-alumina, chlorided silica-alumina; fluorided silica-alumina; sulfated silica-alumina; bromided silica-zirconia; chlorided silica-zirconia; fluorided silica-zirconia; sulfated silica-zirconia; chlorided zinc-alumina; triflate treated silica-alumina; fluorided silica-titania, silica treated with fluoroborate, a pillared clay, such as a pillared montmorillonite, optionally treated with fluoride, chloride, or sulfate; phosphated alumina, or other aluminophosphates, optionally treated with sulfate, fluoride, or chloride; or any combination thereof. Further, any of the activator-supports may optionally be treated with another metal ion, typically from a metal salt or compound, wherein the metal ion may be the same as or different from any metal that makes up the solid oxide material.

The treated oxide activator-support may include a fluorided solid oxide in the form of a particulate solid, thus a source of fluoride ion may be added to the oxide by treatment with a fluoriding agent. For example, fluoride ion may be added to the oxide by forming a slurry of the oxide in a suitable solvent such as alcohol or water, including, for example, alcohols having one to three carbon alcohols. Such alcohols may be selected due to their volatility and low surface tension. Alternatively, the fluoriding source may be dry-mixed with the solid oxide prior to calcining Examples of fluoriding agents that may be used in the present techniques include hydrofluoric acid (HF), ammonium fluoride ($NH_4F$), ammonium bifluoride ($NH_4HF_2$), ammonium tetrafluoroborate ($NH_4BF_4$), ammonium silicofluoride (hexafluorosilicate) (($NH_4$)$_2SiF_6$), ammonium hexafluorophosphate ($NH_4PF_6$), tetrafluoroboric acid ($HBF_4$), ammonium hexafluorotitanate ($NH_4$)$_2TiF_6$, ammonium hexafluorozirconate ($NH_4$)$_2ZrF_6$, analogs thereof, and combinations thereof. A specific fluoriding agent, ammonium bifluoride $NH_4HF_2$, is often used due to its ease of use and ready availability.

The solid oxide may be treated with a fluoriding agent during the calcining step. Any fluoriding agent capable of thoroughly contacting the solid oxide during the calcining step may be used. For example, in addition to those fluoriding agents described previously, volatile organic fluoriding agents may be used. Such volatile organic fluoriding agents that may be used in embodiments include, for example, freons, perfluorohexane, perfluorobenzene, fluoromethane, trifluoroethanol, and combinations thereof. Gaseous hydrogen fluoride or fluorine itself may also be used with the solid oxide is fluorided during calcining. One convenient method of contacting the solid oxide with the fluoriding agent may be to vaporize a fluoriding agent into a gas stream used to fluidize the solid oxide during calcination.

Similarly, the chemically-treated solid oxide may include a chlorided solid oxide in the form of a particulate solid, thus a source of chloride ion may be added to the oxide by treatment with a chloriding agent. The chloride ion may be added to the oxide by forming a slurry of the oxide in a suitable solvent. The solid oxide may also be treated with a chloriding agent during the calcining step. Any chloriding agent that may be capable of serving as a source of chloride and thoroughly contacting the oxide during the calcining step may be used. For example, volatile organic chloriding agents may be used. Examples of such volatile organic chloriding agents include, for example, certain freons, perchlorobenzene, chloromethane, dichloromethane, chloroform, carbon tetrachloride, trichloroethanol, or volatile metal chlorides like $SiCl_4$, $AlCl_3$, $TiCl_4$, $ZrCl_4$, $BCl_3$, $SnCl_4$, etc. or any combination thereof. Gaseous hydrogen chloride or chlorine itself may also be used with the solid oxide during calcining. One convenient method of contacting the oxide with the chloriding agent may be to vaporize a chloriding agent into a gas stream used to fluidize the solid oxide during calcination.

e. Concentration of Electron-Withdrawing Anions

When the activator-support includes a chemically-treated solid oxide including a solid oxide treated with an electron-withdrawing anion, the electron withdrawing anion may be added to the solid oxide in an amount greater than about 1% by weight of the solid oxide. The electron withdrawing anion may be added to the solid oxide in an amount greater than about 2% by weight of the solid oxide, greater than about 3% by weight of the solid oxide, greater than about 5% by weight of the solid oxide, or greater than about 7% by weight of the solid oxide.

The amount of electron-withdrawing ion, for example fluoride or chloride ion, present before calcining the solid oxide may be from about 1 to about 50% by weight, where the weight percents are based on the weight of the solid oxide, for example silica-alumina, before calcining. The amount of electron-withdrawing ion, for example fluoride or chloride ion, present before calcining the solid oxide may be from about 3 to about 25% by weight or from about 4 to about 20% by weight. Alternatively, halide ion or may be used in an amount sufficient to deposit, after calcining, from about 0.1% to about 50%, from about 0.5% to about 40%, or from about 1% to about 30% by weight halide ion relative to the weight of the solid oxide. If the fluoride or chloride ion is added during calcining, such as when calcined in the presence of $CCl_4$, there may be typically no, or only trace levels, of fluoride or chloride ion in the solid oxide before calcining Once impregnated with halide, the halided oxide may be dried by any method. Such methods may include, for example, suction filtration followed by evaporation, drying under vacuum, spray drying, and the like. It may also be possible to initiate the calcining step immediately without drying the impregnated solid oxide.

The silica-alumina used to prepare the treated silica-alumina may have a pore volume greater than about 0.5 cc/g. Alternatively, the pore volume may be greater than about 0.8 cc/g, or greater than about 1.0 cc/g. Further, the silica-alumina may have a surface area greater than about 100 $m^2/g$, 250 $m^2/g$, or 350 $m^2/g$. Generally, the silica-alumina of the present techniques may have an alumina content from about 5 to about 95%. Alternatively, the alumina content of the silica-alumina may be from about 5 to about 50%, or from about 8% to about 30% alumina by weight.

The sulfated solid oxide may include sulfate and a solid oxide component such as alumina or silica-alumina, in the form of a particulate solid. Optionally, the sulfated oxide may be further treated with a metal ion such that the calcined sulfated oxide may include a metal. For example, the sulfated solid oxide may include sulfate and alumina. The sulfated alumina may be formed by a process wherein the alumina is treated with a sulfate source, including, for example, sulfuric acid or a sulfate salt such as ammonium sulfate, zinc sulfate, aluminum sulfate, nickel sulfate or copper sulfate, among others. In embodiments, this process may be performed by forming a slurry of the alumina in a suitable solvent such as alcohol or water, in which the desired concentration of the sulfating agent has been added. Suitable organic solvents include, for example, the one to three carbon alcohols because of their volatility and low surface tension. Alternatively the sulfate salt, such as ammonium bisulfate, can be dry mixed with the alumina before calcining.

The amount of sulfate ion present before calcining may be from about 1% to about 50% by weight, from about 2% to about 30% by weight, or from about 5% to about 25% by weight, where the weight percents are based on the weight of the solid oxide before calcining. Once impregnated with sulfate, the sulfated oxide may be dried by any method including, but not limited to, suction filtration followed by evaporation, drying under vacuum, spray drying, and the like, although it may also be possible to initiate the calcining step immediately.

In addition to being treated with an electron-withdrawing component such as halide or sulfate ion, the solid inorganic oxide of the present techniques may be treated with a metal source, including metal salts or metal-containing compounds. These compounds may be added to or impregnated onto the solid oxide in solution form, and subsequently converted into the supported metal upon calcining. Accordingly, the solid inorganic oxide may further include zinc, nickel, vanadium, silver, copper, gallium, tin, tungsten, molybdenum, or a combination thereof. For example, zinc may be used to impregnate the solid oxide because it provides good catalyst activity and low cost. The solid oxide may be treated with metal salts or metal-containing compounds before, after, or at the same time that the solid oxide may be treated with the electron-withdrawing anion.

Further, any method of impregnating the solid oxide material with a metal may be used. The method by which the oxide is contacted with a metal source, typically a salt or metal-containing compound, may include, for example, gelling, co-gelling, impregnation of one compound onto the other, and similar techniques. Following any contacting method, the contacted mixture of oxide compound, electron-withdrawing anion, and the metal ion may be calcined. Alternatively, a solid oxide material, an electron-withdrawing anion source, and the metal salt or metal-containing compound may be contacted and calcined simultaneously.

The ansa-metallocene compound may be contacted with an olefin monomer and an organoaluminum cocatalyst for a first period of time prior to contacting this mixture with an acidic activator-support. Once the precontacted mixture of metallocene, monomer, and a component that provides an activatable ligand to the metallocene, e.g., an organoaluminum cocatalyst, is contacted with the acidic activator-support, the composition may be termed the "postcontacted" mixture. The postcontacted mixture may be allowed to remain in further contact for a second period of time prior to being charged into the reactor in which the polymerization process will be carried out.

Various processes to prepare solid oxide activator-supports that may be used in the present techniques have been reported. For example, U.S. Pat. Nos. 6,107,230, 6,165,929, 6,294,494, 6,300,271, 6,316,553, 6,355,594, 6,376,415, 6,391,816, 6,395,666, 6,524,987, and 6,548,441, describe such methods, each of which is incorporated by reference in its entirety herein.

3. Ion-Exchangeable and Layered Mineral Activator-Supports

The activator-support of the present techniques may include clay minerals having exchangeable cations and layers capable of expanding. These activator supports include ion-exchangeable materials, such as, for example, silicate and aluminosilicate compounds or minerals, either with layered or non-layered structures, and any combination thereof. Typical clay mineral activator-supports include layered aluminosilicates such as pillared clays. Although the term "support" may be used, it is not meant to be construed as an inert component of the catalyst composition, but rather may be considered an active part of the catalyst composition, because of its intimate association with the ansa-metallocene and the component that provides an activatable ligand to the metallocene, such as an organoaluminum. While not intending to be bound by theory, it is believed that the ion exchangeable activator-support may serve as an insoluble reactant that reacts with the ansa-metallocene and organoaluminum components to form a catalyst composition used to produce polymer. When the acidic activator-support includes an ion-exchangeable activator-support, it may optionally be treated with an electron-withdrawing anion such as those discussed above, though typically the ion-exchangeable activator-support is not treated with an electron-withdrawing anion.

The clay materials of the present techniques may encompass materials either in their natural state or that have been treated with various ions by wetting, ion exchange, or pillaring. The clay material activator-support of the present techniques may include clays that have been ion exchanged with large cations, including polynuclear, highly charged metal complex cations. However, the clay material activator-supports of the present techniques also encompass clays that have been ion exchanged with simple salts, including, but not limited to, salts of Al(III), Fe(II), Fe(III) and Zn(II) with ligands such as halide, acetate, sulfate, nitrate, or nitrite.

The clay activator-support of the present techniques may include pillared clays. The term pillared clays may be used to refer to clay materials that have been ion exchanged with large, typically polynuclear, highly charged metal complex cations. Examples of such ions include, for example, Keggin ions which may have charges such as 7+, various polyoxometallates, and other large ions. Thus, the term pillaring refers to a simple exchange reaction in which the exchangeable cations of a clay material may be replaced with large, highly charged ions, such as Keggin ions. These polymeric cations may then be immobilized within the interlayers of the clay and when calcined are converted to metal oxide "pillars," effectively supporting the clay layers as column-like structures. Thus, once the clay is dried and calcined to produce the supporting pillars between clay layers, the expanded lattice structure may be maintained, enhancing the porosity. The resulting pores can vary in shape and size as a function of the pillaring material and the parent clay material used.

The pillaring process utilizes clay minerals having exchangeable cations and layers capable of expanding. Any pillared clay that can enhance the polymerization of olefins in the catalyst composition of the present techniques may be used. Therefore, suitable clay minerals for pillaring may include, for example: allophanes; smectites, including dioctahedral (Al) and tri-octahedral (Mg) smectites and derivatives thereof, such as, montmorillonites (bentonites), nontronites, hectorites, or laponites; halloysites; vermiculites; micas; fluoromicas; chlorites; mixed-layer clays; the fibrous clays such as sepiolites and attapulgites (palygorskites); serpentine clays; illite; laponite; saponite; or any combination thereof. In one embodiment, the pillared clay activator-support may include bentonite or montmorillonite, noting that the principal component of bentonite is montmorillonite.

The ion-exchangeable activator-supports such as pillared clays used to prepare the catalyst compositions of the present techniques may be combined with other inorganic support materials, including, for example, zeolites, inorganic oxides, phosphated inorganic oxides, and the like. In embodiments, typical support materials that may be used in this regard include, for example, silica, silica-alumina, alumina, titania, zirconia, magnesia, boria, fluorided alumina, silated alumina, thoria, aluminophosphate, aluminum phosphate, zinc aluminate, phosphated silica, phosphated alumina, silica-titania, coprecipitated silica/titania, fluorided/silated alumina, and any combination or mixture thereof. The amount of ansa-metallocene compound in relation to the ion-exchangeable activator-support used to prepare the catalyst composition of the present techniques may be from about 0.1 wt % to about 15 wt % ansa-metallocene complex, based on the weight of the activator-support component (not based on the final metallocene-clay mixture), or from about 1 wt % to about 10 wt % ansa-metallocene.

The mixture of ansa-metallocene and clay activator-support may be contacted and mixed for any length of time sufficient to allow thorough interaction between the ansa-metallocene and activator-support. Sufficient deposition of the metallocene component on the clay may be achieved without heating a mixture of clay and metallocene complex. For example, the ansa-metallocene compound and the clay material may be simply mixed at a temperature range from about room temperature to about 200° F. in order to achieve the deposition of the ansa-metallocene on the clay activator-support. Alternatively, the ansa-metallocene compound and the clay material may be mixed from about 100° F. to about 180° F. in order to achieve the deposition of the ansa-metallocene on the clay activator-support.

The present techniques encompass catalyst compositions including an acidic activator-support, which may include a layered mineral. The term "layered mineral" is used herein to describe materials such as clay minerals, pillared clays, ion-exchanged clays, exfoliated clays, exfoliated clays gelled into another oxide matrix, layered minerals mixed or diluted with other materials, and the like, or any combination thereof. When the acidic activator-support includes a layered mineral, it may optionally be treated with an electron-withdrawing anion such as those presented herein, though typically the layered mineral is not treated with an electron-withdrawing anion. For example, a clay mineral may be used as the activator-support.

Clay minerals generally include the large group of finely-crystalline, sheet-like layered minerals that are found in nature in fine-grained sediments, sedimentary rocks, and the like, and which constitute a class of hydrous silicate and aluminosilicate minerals with sheet-like structures and very high surface areas. This term may also be used to describe hydrous magnesium silicates with a phyllosilicate structure. Examples of clay minerals that may be used in the present techniques include, for example, allophanes; smectites, including dioctahedral (Al) and tri-octahedral (Mg) smectites and derivatives thereof such as montmorillonites (bentonites), nontronites, hectorites, or laponites; halloysites; vermiculites; micas; fluoromicas; chlorites; mixed-layer clays; the fibrous clays, such as sepiolites and attapulgites (palygorskites); a serpentine clay; illite; laponite; saponite; or any combination thereof. Many common clay minerals belong to the kaolinite, montmorillonite, or illite groups of clays.

When layered minerals are used as activator-supports or metallocene activators, the layered minerals may be calcined prior to their use as activators. Typical calcination temperatures may range from about 100° C. to about 700° C., from about 150° C. to about 500° C., or from about 200° C. to about 400° C.

4. Organoaluminoxane Activators/Cocatalysts

The present techniques may include catalyst compositions that use organoaluminoxane compounds as activators and/or cocatalysts. In these embodiments, the catalyst composition may not require an acidic activator-support such as a chemically-treated solid oxide to weaken the bonds between the metal and the $X^3$ or $X^4$ ligands, as the organoaluminoxane may perform this function, or may replace the $X^3$ or $X^4$ ligands with more active species. The catalyst composition may also not require an organoaluminum compound. Thus, any ansa-metallocene compounds presented herein may be combined with any of the aluminoxanes presented herein, or any combination of aluminoxanes presented herein, to form catalyst compositions of the present techniques. Further, any ansa-metallocene compounds presented herein may be combined with any aluminoxane or combination of aluminoxanes, and optionally an activator-support such as, for example, a layered mineral, an ion-exchangeable activator-support, an organoboron compound or an organoborate compound, to form a catalyst composition of the present techniques.

Aluminoxanes may be referred to as poly(hydrocarbyl aluminum oxides) or organoaluminoxanes. The other catalyst components may be contacted with the aluminoxane in a saturated hydrocarbon compound solvent, though any solvent which may be substantially inert to the reactants, intermediates, and products of the activation step may be used. The catalyst composition formed in this manner may be collected by any methods, including but not limited to filtration, or the catalyst composition may be introduced into the polymerization reactor without being isolated.

The aluminoxane compound of the present techniques may be an oligomeric aluminum compound, wherein the aluminoxane compound may include linear structures, cyclic, or cage structures, or mixtures of all three. Cyclic aluminoxane compounds having the formula:

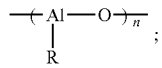

wherein
R may be a linear or branched alkyl having from 1 to 10 carbon atoms, and n may be an integer from 3 to about 10 may be encompassed by the present techniques. The $(AlRO)_n$ moiety shown here also constitutes the repeating unit in a linear aluminoxane. Thus, linear aluminoxanes having the formula:

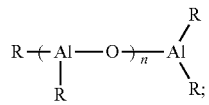

wherein
R may be a linear or branched alkyl having from 1 to 10 carbon atoms, and n may be an integer from 1 to about 50, are also encompassed by the present techniques.

Further, aluminoxanes may also have cage structures of the formula $R^t_{5m+\alpha}R^b_{m-\alpha}Al_{4m}O_{3m}$, wherein m may be 3 or 4 and $\alpha$ is equal to $n_{Al(3)}-n_{O(2)}+n_{O(4)}$. In this structure $n_{Al(3)}$ is the number of three coordinate aluminum atoms, $n_{O(2)}$ is the number of two coordinate oxygen atoms, and $n_{O(4)}$ is the number of 4 coordinate oxygen atoms. $R^t$ represents a terminal alkyl group and $R^b$ represents a bridging alkyl group, either of which may have from 1 to 10 carbon atoms.

Thus, aluminoxanes may be represented generally by formulas such as $(R—Al—O)_n$, $R(R—Al—O)_nAlR_2$, and the like, wherein the R group may be a linear or branched $C_1$-$C_6$ alkyl such as methyl, ethyl, propyl, butyl, pentyl, or hexyl, and n may represent an integer from 1 to about 50. The aluminoxane compounds of the present techniques may include, for example, methylaluminoxane, ethylaluminoxane, n-propylaluminoxane, iso-propylaluminoxane, n-butylaluminoxane, t-butylaluminoxane, sec-butylaluminoxane, iso-butylaluminoxane, 1-pentylaluminoxane, 2-pentylaluminoxane, 3-pentylaluminoxane, iso-pentylaluminoxane, neo-pentylaluminoxane, or combinations thereof.

While organoaluminoxanes with different types of R groups are encompassed by the present techniques, methyl aluminoxane (MAO), ethyl aluminoxane, or isobutyl aluminoxane may also be used as cocatalysts used in the compositions of the present techniques. These aluminoxanes may be prepared from trimethylaluminum, triethylaluminum, or triisobutylaluminum, respectively, and may be referred to as poly(methyl aluminum oxide), poly(ethyl aluminum oxide), and poly(isobutyl aluminum oxide), respectively. It is also within the scope of the current techniques to use an aluminoxane in combination with a trialkylaluminum, such as disclosed in U.S. Pat. No. 4,794,096, which is herein incorporated by reference in its entirety.

The present techniques encompass many values of n in the aluminoxane formulas $(R—Al—O)_n$ and $R(R—Al—O)_nAlR_2$. In typical aluminoxanes, n is at least about 3. However, depending upon how the organoaluminoxane is prepared, stored, and used, the value of n may be variable within a single sample of aluminoxane, and such combinations of organoaluminoxanes are encompassed by the methods and compositions of the present techniques.

In embodiments of the present techniques that include the optional aluminoxane, the molar ratio of the aluminum in the aluminoxane to the metallocene in the composition may be from about 1:10 to about 100,000:1, or from about 5:1 to about 15,000:1. The amount of optional aluminoxane added to a polymerization zone may be an amount within a range of about 0.01 mg/L to about 1000 mg/L, from about 0.1 mg/L to about 100 mg/L, or from about 1 mg/L to about 50 mg/L.

Organoaluminoxanes may be prepared by various procedures which are available. Examples of organoaluminoxane preparations are disclosed in U.S. Pat. Nos. 3,242,099 and 4,808,561, each of which is incorporated by reference in its entirety herein. One example of how an aluminoxane may be prepared is as follows. Water may be dissolved in an inert organic solvent and then reacted with an aluminum alkyl compound such as $AlR_3$ to form the desired organoaluminoxane compound. While not intending to be bound by this statement, it is believed that this synthetic method can afford a mixture of both linear and cyclic $(R-Al-O)_n$ aluminoxane species, both of which are encompassed by the present techniques. Alternatively, organoaluminoxanes may be prepared by reacting an aluminum alkyl compound such as $AlR_3$ with a hydrated salt, such as hydrated copper sulfate, in an inert organic solvent.

5. Organoboron and Organoborate Activators/Cocatalysts

The present techniques may also include catalyst compositions that use organoboron or organoborate compounds as activators and/or cocatalysts. Any ansa-metallocene compound presented herein may be combined with any of the organoboron or organoborate cocatalysts presented herein, or any combination of organoboron or organoborate cocatalysts presented herein. This composition may include a component that provides an activatable ligand such as an alkyl or hydride ligand to the metallocene, when the metallocene compound does not already include such a ligand, such as an organoaluminum compound. Further, any ansa-metallocene compounds presented herein may be combined with: any an organoboron or organoborate cocatalyst; an organoaluminum compound; optionally, an aluminoxane; and optionally, an activator-support; to form a catalyst composition of the present techniques.

The term "organoboron" compound may be used to refer to neutral boron compounds, borate salts, or combinations thereof. For example, the organoboron compounds in various embodiments may be a fluoroorgano boron compound, a fluoroorgano borate compound, or a combination thereof. Any fluoroorgano boron or fluoroorgano borate compound may be utilized. The term fluoroorgano boron has its usual meaning to refer to neutral compounds of the form $BY_3$. The term fluoroorgano borate compound also has its usual meaning to refer to the monoanionic salts of a fluoroorgano boron compound of the form $[cation]^+[BY_4]^-$, where Y represents a fluorinated organic group. For convenience, fluoroorgano boron and fluoroorgano borate compounds may be referred to collectively by organoboron compounds, or by either name as the context requires.

Fluoroorgano borate compounds that may be used as cocatalysts in the present techniques include, for example, fluorinated aryl borates such as, N,N-dimethylanilinium tetrakis(pentafluorophenyl)borate, triphenylcarbenium tetrakis(pentafluorophenyl)borate, lithium tetrakis(pentafluorophenyl)borate, N,N-dimethylanilinium tetrakis[3,5-bis(trifluoromethyl)phenyl]borate, triphenylcarbenium tetrakis[3,5-bis(trifluoromethyl)phenyl]borate, and the like, including mixtures thereof. Examples of fluoroorgano boron compounds that may be used as cocatalysts in the present techniques include, for example, tris(pentafluorophenyl)boron, tris[3,5-bis(trifluoromethyl)phenyl]boron, and the like, including mixtures thereof.

Although not intending to be bound by the following theory, these examples of fluoroorgano borate and fluoroorgano boron compounds, and related compounds, are thought to form weakly-coordinating anions when combined with organometal compounds, as disclosed in U.S. Pat. No. 5,919,983, which is herein included by reference in its entirety herein.

Generally, any amount of organoboron compound may be utilized in the present techniques. In some embodiments, the molar ratio of the organoboron compound to the metallocene compound in the composition may be from about 0.1:1 to about 10:1, or from about 0.5 mole to about 10 moles of boron compound per mole of metallocene compound. In embodiments, the amount of fluoroorgano boron or fluoroorgano borate compound used as a cocatalyst for the metallocene may range of from about 0.8 mole to about 5 moles of boron compound per mole of metallocene compound.

6. Ionizing Ionic Compound Activators/Cocatalysts

Embodiments of the present techniques may include a catalyst composition as presented herein, that also includes an optional ionizing ionic compound as an activator and/or cocatalyst in addition to other components. Examples of such ionizing ionic compounds are disclosed in U.S. Pat. Nos. 5,576,259 and 5,807,938 which are herein incorporated by reference in their entirety herein.

An ionizing ionic compound is an ionic compound which can function to enhance activity of the catalyst composition. While not intending to be bound by theory, it is believed that the ionizing ionic compound may be capable of reacting with the metallocene compound and converting the metallocene into a cationic metallocene compound. Again, while not intending to be bound by theory, it is believed that the ionizing ionic compound can function as an ionizing compound by completely or partially extracting an anionic ligand, such as one of the non-$\eta^5$-alkadienyl ligands, $X^3$ or $X^4$, from the metallocene. However, the ionizing ionic compound is an activator regardless of whether it is ionizes the metallocene, abstracts an $X^3$ or $X^4$ ligand in a fashion as to form an ion pair, weakens the metal-$(X^3)$ or metal-$(X^4)$ bond in the metallocene, simply coordinates to an $X^3$ or $X^4$ ligand, or any other mechanisms by which activation can occur. Further, it is not necessary that the ionizing ionic compound activate the metallocene only. The activation function of the ionizing ionic compound may be evident in the enhanced activity of catalyst composition as a whole, as compared to a catalyst composition containing catalyst composition that does not include any ionizing ionic compound.

Examples of ionizing ionic compounds may include, for example, such compounds as: tri(n-butyl)ammonium tetrakis(p-tolyl)borate, tri(n-butyl)ammonium tetrakis(m-tolyl)borate, tri(n-butyl)ammonium tetrakis(2,4-dimethylphenyl)borate, tri(n-butyl)ammonium tetrakis(3,5-dimethylphenyl)borate, tri(n-butyl)ammonium tetrakis[3,5-bis(trifluoromethyl)phenyl]borate, tri(n-butyl)ammonium tetrakis(pentafluorophenyl)borate, N,N-dimethylanilinium tetrakis(p-tolyl)borate, N,N-dimethylanilinium tetrakis(m-tolyl)borate, N,N-dimethylanilinium tetrakis(2,4-dimethylphenyl)borate, N,N-dimethylanilinium tetrakis(3,5-dimethylphenyl)borate, N,N-dimethylanilinium tetrakis[3,5-bis(trifluoromethyl)phenyl]borate, N,N-dimethylanilinium tetrakis(pentafluorophenyl)borate, triphenylcarbenium tetrakis(p-tolyl)borate, triphenylcarbenium tetrakis(m-tolyl)borate, triphenylcarbenium tetrakis(2,4-dimethylphenyl)borate, triphenylcarbenium tetrakis(3,5-dimethylphenyl)borate, triphenylcarbenium tetrakis[3,5-bis(trifluoromethyl)phenyl]borate, triphenylcarbenium tetrakis(pentafluorophenyl)borate, tropylium tetrakis(p-tolyl)borate, tropylium tetrakis(m-tolyl)borate, tropylium tetrakis(2,4-dimethylphenyl)borate, tropylium tetrakis(3,5-dimethylphenyl)borate, tropylium tetrakis[3,5-bis(trifluoromethyl)phenyl]borate, tropylium tetrakis(pentafluorophenyl)borate, lithium tetrakis(pentafluorophenyl)borate, lithium tetrakis(phenyl)borate, lithium tetrakis(p-tolyl)borate, lithium tetrakis(m-tolyl)borate, lithium tetrakis(2,4-dimethylphenyl)borate, lithium tetrakis(3,5-dimethylphenyl)borate, lithium tetrafluoroborate, sodium tetrakis(pentafluoro-phenyl)borate, sodium tetrakis(phenyl)borate, sodium tetrakis(p-tolyl)

borate, sodium tetrakis(m-tolyl)borate, sodium tetrakis(2,4-dimethylphenyl)borate, sodium tetrakis(3,5-dimethylphenyl)borate, sodium tetrafluoroborate, potassium tetrakis-(pentafluorophenyl)borate, potassium tetrakis(phenyl)borate, potassium tetrakis(p-tolyl)borate, potassium tetrakis(m-tolyl)borate, potassium tetrakis(2,4-dimethyl-phenyl)borate, potassium tetrakis(3,5-dimethylphenyl)borate, potassium tetrafluoro-borate, triphenylcarbenium tetrakis(p-tolyl)aluminate, triphenylcarbenium tetrakis(m-tolyl)aluminate, triphenylcarbenium tetrakis(2,4-dimethylphenyl)aluminate, triphenyl-carbenium tetrakis(3,5-dimethylphenyl)aluminate, triphenylcarbenium tetrakis-(pentafluorophenyl)aluminate, tropylium tetrakis(p-tolyl)aluminate, tropylium tetrakis(m-tolyl)aluminate, tropylium tetrakis(2,4-dimethylphenyl)aluminate, tropylium tetrakis(3,5-dimethylphenyl)aluminate, tropylium tetrakis(pentafluorophenyl)aluminate, lithium tetrakis(pentafluorophenyl)aluminate, lithium tetrakis(phenyl)aluminate, lithium tetrakis(p-tolyl)aluminate, lithium tetrakis(m-tolyl)aluminate, lithium tetrakis(2,4-dimethylphenyl)aluminate, lithium tetrakis(3,5-dimethylphenyl)aluminate, lithium tetrafluoroaluminate, sodium tetrakis (pentafluorophenyl)aluminate, sodium tetrakis(phenyl)aluminate, sodium tetrakis(p-tolyl)aluminate, sodium tetrakis(m-tolyl)aluminate, sodium tetrakis(2,4-dimethylphenyl)aluminate, sodium tetrakis(3,5-dimethylphenyl) aluminate, sodium tetrafluoroaluminate, potassium tetrakis (pentafluorophenyl)aluminate, potassium tetrakis(phenyl) aluminate, potassium tetrakis(p-tolyl)aluminate, potassium tetrakis(m-tolyl)aluminate, potassium tetrakis(2,4-dimethylphenyl)aluminate, potassium tetrakis (3,5-dimethylphenyl) aluminate, potassium tetrafluoroaluminate, triphenylcarbenium tris(2,2',2"-nonafluorobiphenyl)fluoroaluminate, silver tetrakis(1,1,1,3,3,3-hexafluoro-isopropanolato)aluminate, or silver tetrakis(perfluoro-t-butoxy)aluminate, or any combination thereof.

D. Non-Limiting Examples of the Catalyst Composition

Exemplary catalyst compositions of the present techniques may include the compositions described below. In embodiments, for example, the catalyst composition may include, or the catalyst composition may include the contact product of, an ansa-metallocene, an organoaluminum compound, and an activator-support. The ansa-metallocene may include compounds having the general formula:

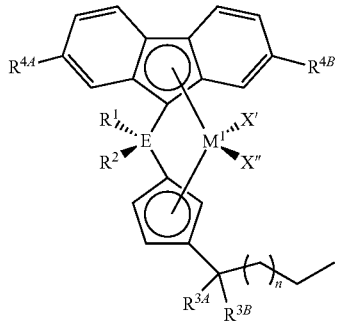

In this formula, $M^1$ may be zirconium or hafnium and X' and X" may be independently F, Cl, Br, or I. E may be C or Si and $R^1$ and $R^2$ may be independently an alkyl group or an aryl group, either of which having up to 10 carbon atoms, or hydrogen. $R^{3A}$ and $R^{3B}$ may be independently a hydrocarbyl group or a trihydrocarbylsilyl group, any of which having up to 20 carbon atoms, or hydrogen. The subscript 'n' may be an integer from 0 to 10, inclusive. $R^{4A}$ and $R^{4B}$ may be independently a hydrocarbyl group having up to 12 carbon atoms, or hydrogen. The organoaluminum compound may be, for example, trimethylaluminum, triethylaluminum, tripropylaluminum, tributylaluminum, triisobutylaluminum, trihexylaluminum, triisohexylaluminum, trioctylaluminum, diethylaluminum ethoxide, diisobutylaluminum hydride, diethylaluminum chloride, or any combination thereof. In this embodiment, the activator-support may be a solid oxide treated with an electron-withdrawing anion, wherein the solid oxide may be, for example, silica, alumina, silica-alumina, aluminophosphate, aluminum phosphate, zinc aluminate, heteropolytungstates, titania, zirconia, magnesia, boria, zinc oxide, mixed oxides thereof, or any combination thereof. The electron-withdrawing anion may be, for example, fluoride, chloride, bromide, iodide, phosphate, triflate, bisulfate, sulfate, fluoroborate, fluorosulfate, trifluoroacetate, phosphate, fluorophosphate, fluorozirconate, fluorosilicate, fluorotitanate, permanganate, substituted or unsubstituted alkanesulfonate, substituted or unsubstituted arenesulfonate, substituted or unsubstituted alkylsulfate, or any combination thereof.

Alternatively, in the embodiments described above, the ansa-metallocene may be compounds having the general formula:

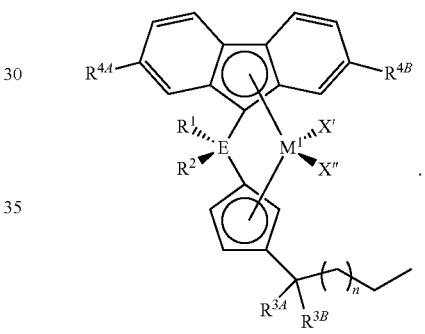

In this formula, $M^1$ may be zirconium or hafnium and X' and X" may be independently F, Cl, Br, or I. E may be C or Si and $R^1$ and $R^2$ may be independently an alkyl group or an aryl group, either of which having up to 10 carbon atoms, or hydrogen. $R^{3A}$ and $R^{3B}$ may be independently H, methyl, ethyl, allyl, benzyl, butyl, pentyl, hexyl, or trimethylsilyl. The subscript 'n' may be an integer from 1 to 6, inclusive. $R^{4A}$ and $R^{4B}$ may be independently a hydrocarbyl group having up to 6 carbon atoms, or hydrogen.

Further, in the embodiments described above, the ansa-metallocene may be compounds having the general formula:

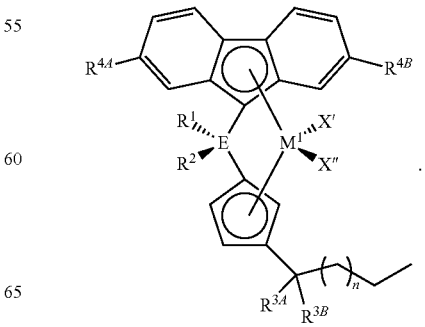

In this formula, $M^1$ may be zirconium or hafnium and X' and X" may be independently F, Cl, Br, or I. E may be C or Si and $R^1$ and $R^2$ may be independently methyl or phenyl. $R^{3A}$ and $R^{3B}$ may be independently H or methyl, and the subscript 'n' may be 1 or 2. $R^{4A}$ and $R^{4B}$ may be independently H or t-butyl. For example, in the catalyst composition described above, the ansa-metallocene may be any of (I-1) through (I-4), as shown in FIG. 1, or any combination thereof.

In exemplary embodiments, the catalyst composition may include, or the catalyst composition may include the contact product of, an ansa-metallocene, an organoaluminum compound, and an activator-support. The ansa-metallocene may be any of (I-1) through (I-4), as shown in FIG. 1, or any combination thereof. The organoaluminum compound may include triethylaluminum, tri-n-butylaluminum, triisobutylaluminum, or any combination thereof. The activator-support may include a sulfated solid oxide.

In other embodiments, the catalyst composition may include, or the catalyst composition may include the contact product of, an ansa-metallocene, an organoaluminum compound, and an activator-support. In these embodiments the ansa-metallocene may be any of (I-1) through (I-4), as shown in FIG. 1, or any combination thereof. The organoaluminum compound may include triethylaluminum, tri-n-butylaluminum, triisobutylaluminum, or any combination thereof. The activator-support may include sulfated alumina.

In yet other embodiments, the catalyst composition may include, or the catalyst composition may include the contact product of a precontacted ansa-metallocene, a precontacted organoaluminum compound, a precontacted olefin, and a postcontacted activator-support, wherein each of the ansa-metallocene, the organoaluminum compound, the olefin, and the activator-support may be as presented herein.

Further embodiments of the present techniques provide a catalyst composition that includes the contact product of a tightly-bridged ansa-metallocene compound containing an alkyl group attached to the $\eta^5$-cyclopentadienyl-type ligand and a reagent that can function to convert the metallocene into an active catalyst that is different from the combination of the solid oxide activator-support and organoaluminum compound presented herein. Thus, in one embodiment, the active catalyst composition may be formed by activating the metallocene, which may include converting the metallocene compound to its cationic form, and by providing it with a hydrocarbyl ligand (e.g., alkylation) before, after, or during its conversion to a cation that can initiate olefin polymerization. The reagent that can convert the metallocene into an active catalyst may include a component that provides an activatable ligand such as an alkyl to the metallocene and an activator component, as provided herein. In some instances, both functions may be achieved with one component, for example, an organoaluminoxane. In other instances, these two functions may be provided by two separate components, such as an organoaluminum compound that can provide an activatable alkyl ligand to the metallocene, and another component that can provide the activator function.

The activator and/or alkylation agent for the ansa-metallocene compound may be an organoaluminoxane, such as, for example, methylaluminoxane or isobutylaluminoxane. Alternatively, the activator may be a Lewis acidic organoboron compound capable of abstracting an anionic ligand from the metallocene, such as, for example, tris(pentafluorophenyl) boron or triphenylcarbenium tetrakis(pentafluorophenyl)borate, that may be used in combination with an alkylating agent such as an organoaluminum compound.

Further, a dialkylated tightly-bridged ansa-metallocene compound as presented herein may be reacted with a Brøn- sted acidic borate activator such as tri(n-butyl)ammonium tetrakis(p-tolyl)borate or N,N-dimethylanilinium tetrakis-(pentafluorophenyl)borate to remove one alkyl ligand to form an alkylated metallocene cation. Alternatively, the dialkylated tightly-bridged ansa-metallocene compound may be reacted with a Lewis acid borate activator such as triphenylcarbenium tetrakis(pentafluorophenyl)borate to remove one alkyl ligand to form an alkylated metallocene cation. Thus, while not intending to be bound by theory, it is believed that the active catalyst may include an alkylated metallocene cation, and any number of alternate reactions may be used to generate such a catalyst.

The present techniques may include a catalyst composition that contains a contact product of a tightly-bridged ansa-metallocene which includes a hydrocarbyl ligand that can initiate olefin polymerization and a solid oxide activator-support, without the need for the addition of an organoaluminum compound. The ansa-metallocene compound may include a pendant alkyl group attached to one of the $\eta^5$-cyclopentadienyl-type ligand, and a hydrocarbyl ligand that can initiate olefin polymerization. An organoaluminum compound may not be required to alkylate this type of "pre-alkylated" ansa-metallocene because it already includes a hydrocarbyl ligand that can initiate olefin polymerization.

E. The Olefin Monomer

In the present techniques, various unsaturated reactants may be useful in the polymerization processes with catalyst compositions and processes. Such reactants include olefin compounds having from about 2 to about 30 carbon atoms per molecule and having an olefinic double bond. The present techniques encompass homopolymerization processes using a single olefin such as ethylene or propylene, as well as copolymerization reactions with two or more different olefinic compounds. For example, in a copolymerization reaction with ethylene, copolymers may include a major amount of ethylene (>50 mole percent) and a minor amount of comonomer <50 mole percent. The comonomers that may be copolymerized with ethylene may have from three to about 20 carbon atoms in their molecular chain.

Olefins that may be used as monomer or comonomer include acyclic, cyclic, polycyclic, terminal ($\alpha$), internal, linear, branched, substituted, unsubstituted, functionalized, and non-functionalized olefins. For example, compounds that may be polymerized with the catalysts of the present techniques include propylene, 1-butene, 2-butene, 3-methyl-1-butene, isobutylene, 1-pentene, 2-pentene, 3-methyl-1-pentene, 4-methyl-1-pentene, 1-hexene, 2-hexene, 3-hexene, 3-ethyl-1-hexene, 1-heptene, 2-heptene, 3-heptene, the four normal octenes, the four normal nonenes, the five normal decenes, or any combination thereof. Further, cyclic and bicyclic olefins, including, for example, cyclopentene, cyclohexene, norbornylene, norbornadiene, and the like, may also be polymerized as described above.

The amount of comonomer introduced into a reactor zone to produce a copolymer may be from about 0.001 to about 99 weight percent comonomer based on the total weight of the monomer and comonomer, generally from about 0.01 to about 50 weight percent. In other embodiments, the amount of comonomer introduced into a reactor zone may be from about 0.01 to about 10 weight percent comonomer or from about 0.1 to about 5 weight percent comonomer. Alternatively, an amount sufficient to give the above described concentrations, by weight, of the copolymer produced, may be used.

While not intending to be bound by theory, it is believed that steric hindrance can impede or slow the polymerization process if branched, substituted, or functionalized olefins are used as reactants. However, if the branched and/or cyclic portion(s) of the olefin are somewhat removed from the carbon-carbon double bond they would not be expected to hinder the reaction as much as more proximate substituents.

In exemplary embodiments, a reactant for the catalyst compositions of the present techniques is ethylene, so the polymerizations may be either homopolymerizations or copolymerizations with a different acyclic, cyclic, terminal, internal, linear, branched, substituted, or unsubstituted olefin. In addition, the catalyst compositions of the present techniques may be used in polymerization of diolefin compounds, including for example, such compounds as 1,3-butadiene, isoprene, 1,4-pentadiene, and 1,5-hexadiene.

II. Preparation of the Catalyst Composition

The present techniques encompass a catalyst composition and a method that includes contacting a tightly-bridged ansa-metallocene compound, an activator, and optionally an organoaluminum compound, as presented herein. The method presented herein encompasses any series of contacting steps that allows contacting each of the components including any order of contacting components or mixtures of components. While not intending to be limiting, examples of contacting steps may be exemplified using a treated solid oxide activator-support and an organoaluminum cocatalyst. These steps may encompass any number of precontacting and postcontacting steps, and may further encompass using an olefin monomer as a contact component in any of these steps. Examples of methods to prepare the catalyst composition of the present techniques are discussed below.

A. Precontacting the Catalyst Composition with an Olefin

Precontacting a catalyst composition, or a component of a catalyst composition, with an olefinic monomer prior to adding the catalyst composition to a reactor may increase the productivity of the polymer as compared to the same catalyst composition that is prepared without a precontacting step. The enhanced activity catalyst composition of the present techniques may be used for homopolymerization of an α-olefin monomer such as ethylene or copolymerization of an α-olefin and a comonomer. However, a precontacting step is not required for the catalyst compositions of the present techniques.

In some embodiments of the present techniques, the ansa-metallocene may be precontacted with an olefinic monomer, although not necessarily the olefin monomer to be polymerized, and an organoaluminum cocatalyst for a first period of time. This precontacted mixture may then be contacted with the solid oxide activator-support. For example, the first period of time for contact, the precontact time, between the ansa-metallocene, the olefinic monomer, and the organoaluminum cocatalyst may range in time from about 1 minute to about 24 hours, from about 0.1 to about 1 hour, or from about 10 minutes to about 30 minutes.

Once the precontacted mixture of ansa-metallocene, olefin monomer, and organoaluminum cocatalyst is contacted with the solid oxide activator, this composition (further including the solid oxide activator) may be termed the postcontacted mixture. The postcontacted mixture may be allowed to remain in contact for a second period of time, the postcontact time, prior to being used in the polymerization process. This may provide increases in activity in a similar fashion to precontacting the catalyst composition. Postcontact times between the solid oxide activator-support and the precontacted mixture may range in time from about 1 minute to about 24 hours, from 0.1 hours to about 1 hour, or from about 10 minutes to about 30 minutes.

The various catalyst components (for example, ansa-metallocene, activator-support, organoaluminum cocatalyst, and optionally an unsaturated hydrocarbon) may be contacted in the polymerization reactor simultaneously while the polymerization reaction is proceeding. Alternatively, any two or more of these catalyst components may be precontacted in a vessel or tube prior to their entering the reaction zone. This precontacting step may be a continuous process, in which the precontacted product may be fed continuously to the reactor, or it may be a stepwise or batchwise process in which a batch of precontacted product may be added to make a catalyst composition. This precontacting step may be carried out over a time period that may range from a few seconds to as much as several days, or longer. For example, the continuous precontacting step may last from about 1 second to about 1 hour, from about 10 seconds to about 45 minutes, or from about 1 minute to about 30 minutes.

B. Multiple Precontacting Steps

Alternatively the precontacting process may be carried out in multiple steps, rather than a single step, in which multiple mixtures are prepared, each including a different set of catalyst components. For example, at least two catalyst components may be contacted forming a first mixture, followed by contacting the first mixture with another catalyst component forming a second mixture, and so forth.

Multiple precontacting steps may be carried out in a single vessel or in multiple vessels. Further, multiple precontacting steps may be carried out in series (sequentially), in parallel, or a combination thereof. For example, a first mixture of two catalyst components may be formed in a first vessel, a second mixture including the first mixture plus one additional catalyst component may be formed in the first vessel or in a second vessel, which may be placed downstream of the first vessel.

One or more of the catalyst components may be split and used in different precontacting treatments. For example, part of a catalyst component may be fed into a first precontacting vessel for precontacting with another catalyst component, while the remainder of that same catalyst component may be fed into a second precontacting vessel for precontacting with another catalyst component, or may be fed directly into the reactor, or a combination thereof. The precontacting may be carried out in any suitable equipment, such as tanks, stirred mix tanks, various static mixing devices, a tube, a flask, a vessel of any type, or any combination thereof. For example, a catalyst composition of the present techniques may be prepared by contacting 1-hexene, triisobutylaluminum or tri-n-butylaluminum, and an ansa-metallocene for at least about 30 minutes, followed by contacting the precontacted mixture with a sulfated alumina activator-support for at least about 10 minutes up to one hour to form the active catalyst.

The postcontacted mixture may be heated at a temperature and for a time sufficient to allow adsorption, impregnation, or interaction of precontacted mixture and the solid oxide activator-support, such that a portion of the components of the precontacted mixture may be immobilized, adsorbed, or deposited thereon. For example, the postcontacted mixture may be heated from between about 0° F. to about 150° F., or from between about 40° F. to about 95° F. Neither a precontacting step nor a postcontacting step may be required for the present techniques.

C. Composition Ratios for Catalyst Compositions

In embodiments of the present techniques, the molar ratio of the ansa-metallocene compound to the organoaluminum compound may be from about 1:1 to about 1:10,000 (e.g., about 1:2, 1:5, 1:20, 1:50, 1:200, 1:500, 1:2000, 1:5000, 1:8000, etc.), from about 1:1 to about 1:1,000, or from about 1:1 to about 1:100. These molar ratios reflect the ratio of ansa-metallocene compound to the total amount of organoaluminum compound in both the precontacted mixture and the postcontacted mixture, combined.

When a precontacting step is used, the molar ratio of olefin monomer to ansa-metallocene compound in the precontacted mixture may be from about 1:10 to about 100,000:1 (e.g., 1:10, 1:5, 1:1, 5:1, 5000:1, 10,000:1, 50,000:1, etc.), or from about 10:1 to about 1,000:1. The weight ratio of the solid oxide activator to the organoaluminum compound may range from about 1:5 to about 1,000:1, from about 1:3 to about 100:1, or from about 1:1 to about 50:1. The weight ratio of the ansa-metallocene to solid oxide activator-support may be from about 1:1 to about 1:1,000,000 (e.g., 1:2, 1:10, 1:5,000, 1:100,000, etc.), from about 1:10 to about 1:100,000, or from about 1:20 to about 1:1000.

D. Examples of a Process to Prepare a Catalyst Composition

Embodiments of the present techniques include processes to produce a catalyst composition. For example, one such process may include contacting an ansa-metallocene, an olefin, and an organoaluminum compound for a first period of time to form a precontacted mixture including a precontacted ansa-metallocene, a precontacted organoaluminum compound, and a precontacted olefin. The precontacted mixture may then be contacted with an activator-support and optionally additional organoaluminum compound for a second period of time to form a postcontacted mixture including a postcontacted ansa-metallocene, a postcontacted organoaluminum compound, a postcontacted olefin, and a postcontacted activator-support. In embodiments, the ansa-metallocene may include a compound having the formula:

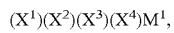

$(X^1)(X^2)(X^3)(X^4)M^1$, in which $M^1$ may be titanium, zirconium, or hafnium. $X^1$ may be a substituted cyclopentadienyl, a substituted indenyl, or a substituted fluorenyl. $X^2$ may be a substituted cyclopentadienyl or a substituted fluorenyl.

One substituent on $X^1$ and $X^2$ is a bridging group having the formula $ER^1R^2$, in which E may be a carbon atom, a silicon atom, a germanium atom, or a tin atom. E is bonded to both $X^1$ and $X^2$. $R^1$ and $R^2$ may be independently an alkyl group or an aryl group, either of which having up to 12 carbon atoms, or hydrogen. One substituent on $X^2$ is a substituted or an unsubstituted alkyl group having up to 12 carbon atoms.

$X^3$ and $X^4$ may be independently: 1) F, Cl, Br, or I; 2) a hydrocarbyl group having up to 20 carbon atoms, H, or $BH_4$; 3) a hydrocarbyloxide group, a hydrocarbylamino group, or a trihydrocarbylsilyl group, any of which having up to 20 carbon atoms; 4) $OBR^A{}_2$ or $SO_3R^A$, wherein $R^A$ may be an alkyl group or an aryl group, any of which having up to 12 carbon atoms.

Any additional substituent on the substituted cyclopentadienyl, substituted indenyl, substituted fluorenyl, or substituted alkyl group may be independently an aliphatic group, an aromatic group, a cyclic group, a combination of aliphatic and cyclic groups, an oxygen group, a sulfur group, a nitrogen group, a phosphorus group, an arsenic group, a carbon group, a silicon group, or a boron group, any of which having from 1 to 20 carbon atoms; a halide; or hydrogen.

E. Activity of the Catalyst Composition

The catalytic activity of the catalyst of the present techniques may be greater than or equal to about 1000 grams polyethylene per gram of chemically treated solid oxide per hour (abbreviated gP/(g CTSO·hr)), greater than or equal to about 3000 gP/(g CTSO·hr), greater than or equal to about 6000 gP/(g CTSO·hr), or greater than or equal to about 9000 gP/(g CTSO·hr). Activity may be measured under slurry polymerization conditions using isobutane as the diluent, with a polymerization temperature from about 80° C. to about 100° C., and an ethylene pressure of about 340 psig to about 450 psig. The reactor should have substantially no indication of any wall scale, coating or other forms of fouling when making these measurements.

III. Use of the Catalyst Composition in Polymerization Processes

The catalysts of the present techniques are intended for any olefin polymerization method, using various types of polymerization reactors. As used herein, "polymerization reactor" includes any polymerization reactor capable of polymerizing olefin monomers to produce homopolymers or copolymers. Such homopolymers and copolymers may be referred to as resins or polymers. The various types of reactors include those that may be referred to as batch, slurry, gas-phase, solution, high pressure, tubular or autoclave reactors. Gas phase reactors may include fluidized bed reactors or staged horizontal reactors. Slurry reactors may include vertical or horizontal loops. High pressure reactors may include autoclave or tubular reactors. Reactor types may include batch or continuous processes. Continuous processes could use intermittent or continuous product discharge. Processes may also include partial or full direct recycle of un-reacted monomer, un-reacted comonomer, and/or diluent.

Polymerization reactor systems of the present techniques may include one type of reactor in a system or multiple reactors of the same or different type. Production of polymers in multiple reactors may include several stages in at least two separate polymerization reactors interconnected by a transfer device making it possible to transfer the polymers resulting from the first polymerization reactor into the second reactor. The desired polymerization conditions in one of the reactors may be different from the operating conditions of the other reactors. Alternatively, polymerization in multiple reactors may include the manual transfer of polymer from one reactor to subsequent reactors for continued polymerization. Multiple reactor systems may include any combination including, but not limited to, multiple loop reactors, multiple gas reactors, a combination of loop and gas reactors, multiple high pressure reactors or a combination of high pressure with loop and/or gas reactors. The multiple reactors may be operated in series or in parallel.

A. Loop Slurry Polymerization Processes

In embodiments of the present techniques, the polymerization reactor system may include a loop slurry reactor. Such reactors may include vertical or horizontal loops. Monomer, diluent, catalyst and optionally any comonomer may be continuously fed to the loop reactor where polymerization occurs. Generally, continuous processes may include the continuous introduction of a monomer, a catalyst, and a diluent into a polymerization reactor and the continuous removal from this reactor of a suspension including polymer particles and the diluent. Reactor effluent may be flashed to remove the solid polymer from the liquids that include the diluent, monomer and/or comonomer. Various technologies may be employed for this separation step including but not limited to, flashing that may include any combination of heat addition and pressure reduction; separation by cyclonic action in either a cyclone or hydrocyclone; or separation by centrifugation.

Loop slurry polymerization processes (also known as the particle form process) are disclosed, for example, in U.S. Pat. Nos. 3,248,179, 4,501,885, 5,565,175, 5,575,979, 6,239,235, 6,262,191 and 6,833,415, each of which is incorporated by reference in its entirety herein.

Diluents that may be used in slurry polymerization include, for example, the monomer being polymerized and hydrocarbons that are liquids under reaction conditions. Examples of such diluents may include, for example, hydrocarbons such as propane, cyclohexane, isobutane, n-butane, n-pentane, isopentane, neopentane, and n-hexane. Some loop polymerization reactions can occur under bulk conditions where no diluent may be used or where the monomer (e.g., propylene) acts as the diluent. An example is polymerization of propylene monomer as disclosed in U.S. Pat. No. 5,455,314, which is incorporated by reference in its entirety herein.

B. Gas Phase Polymerization Processes

Further, the polymerization reactor may include a gas phase reactor. Such systems may employ a continuous recycle stream containing one or more monomers continuously cycled through a fluidized bed in the presence of the catalyst under polymerization conditions. A recycle stream may be withdrawn from the fluidized bed and recycled back into the reactor. Simultaneously, polymer product may be withdrawn from the reactor and new or fresh monomer may be added to replace the polymerized monomer. Such gas phase reactors may include a process for multi-step gas-phase polymerization of olefins, in which olefins are polymerized in the gaseous phase in at least two independent gas-phase polymerization zones while feeding a catalyst-containing polymer formed in a first polymerization zone to a second polymerization zone. One type of gas phase reactor is disclosed in U.S. Pat. Nos. 5,352,749, 4,588,790 and 5,436,304, each of which is incorporated by reference in its entirety herein.

According to still another aspect of the techniques, a high pressure polymerization reactor may include a tubular reactor or an autoclave reactor. Tubular reactors may have several zones where fresh monomer, initiators, or catalysts are added. Monomer may be entrained in an inert gaseous stream and introduced at one zone of the reactor. Initiators, catalysts, and/or catalyst components may be entrained in a gaseous stream and introduced at another zone of the reactor. The gas streams may be intermixed for polymerization. Heat and pressure may be employed appropriately to obtain optimal polymerization reaction conditions.

C. Solution Polymerization Processes

According to yet another aspect of the techniques, the polymerization reactor may include a solution polymerization reactor wherein the monomer is contacted with the catalyst composition by suitable stirring or other means. A carrier including an inert organic diluent or excess monomer may be employed. If desired, the monomer may be brought in the vapor phase into contact with the catalytic reaction product, in the presence or absence of liquid material. The polymerization zone may be maintained at temperatures and pressures that will result in the formation of a solution of the polymer in a reaction medium. Agitation may be employed to obtain better temperature control and to maintain uniform polymerization mixtures throughout the polymerization zone. Adequate means may be utilized for dissipating the exothermic heat of polymerization.

D. Reactor Support Systems

Polymerization reactors suitable for the present techniques may further include any combination of a raw material feed system, a feed system for catalyst or catalyst components, and/or a polymer recovery system. Such systems may include systems for feedstock purification, catalyst storage and preparation, extrusion, reactor cooling, polymer recovery, fractionation, recycle, storage, loadout, laboratory analysis, and process control, among others.

E. Polymerization Conditions

Conditions that may be controlled for polymerization efficiency and to provide resin properties include temperature, pressure and the concentrations of various reactants. Polymerization temperature can affect catalyst productivity, polymer molecular weight and molecular weight distribution. Suitable polymerization temperature may be any temperature below the de-polymerization temperature according to the Gibbs Free energy equation. Typically this includes from about 60° C. to about 280° C., for example, and from about 70° C. to about 110° C., depending upon the type of polymerization reactor.

Suitable pressures will also vary according to the reactor and polymerization type. The pressure for liquid phase polymerizations in a loop reactor is typically less than 1000 psig. Pressure for gas phase polymerization is usually at about 200-500 psig. High pressure polymerization in tubular or autoclave reactors is generally run at about 20,000 to 75,000 psig. Polymerization reactors may also be operated in a supercritical region occurring at generally higher temperatures and pressures. Operation above the critical point of a pressure/temperature diagram (supercritical phase) may offer advantages.

The concentration of various reactants may be controlled to produce resins with certain physical and mechanical properties. The proposed end-use product that will be formed by the resin and the method of forming that product determines the desired resin properties. Mechanical properties include tensile, flexural, impact, creep, stress relaxation and hardness tests. Physical properties include density, molecular weight, molecular weight distribution, melting temperature, glass transition temperature, temperature melt of crystallization, density, stereoregularity, crack growth, long chain branching and rheological measurements.

The concentrations of monomer, co-monomer, hydrogen, co-catalyst, modifiers, and electron donors may be important in producing these resin properties. Comonomer may be used to control product density. Hydrogen may be used to control product molecular weight. Co-catalysts may be used to alkylate, scavenge poisons and control molecular weight. Modifiers may be used to control product properties and electron donors affect stereoregularity. In addition, the concentration of poisons must be minimized since they impact the reactions and product properties.

F. Final Products Made from Polymers

The polymer or resin fluff from the reactor system may have additives and modifiers added to provide better processing during manufacturing and for desired properties in the end product. Additives include surface modifiers such as slip agents, antiblocks, tackifiers; antioxidants such as primary and secondary antioxidants; pigments; processing aids such as waxes/oils and fluoroelastomers; and special additives such as fire retardants, antistats, scavengers, absorbers, odor enhancers, and degradation agents. After the addition of the additives, the polymer or resin fluff may be extruded and formed into pellets for distribution to customers and formation into final end-products.

To form end-products or components from the pellets, the pellets are generally subjected to further processing, such as blow molding, injection molding, rotational molding, blown film, cast film, extrusion (e.g., sheet extrusion, pipe and corrugated extrusion, coating/lamination extrusion, etc.), and so on. Blow molding is a process used for producing hollow plastic parts. The process typically employs blow molding equipment, such as reciprocating screw machines, accumulator head machines, and so on. The blow molding process may be tailored to meet the customer's needs, and to manufacture products ranging from the plastic milk bottles to the automotive fuel tanks mentioned above. Similarly, in injection molding, products and components may be molded for a wide range of applications, including containers, food and chemical packaging, toys, automotive, crates, caps and closures, to name a few.

Profile extrusion processes may also be used. Polyethylene pipe, for example, may be extruded from polyethylene pellet resins and used in an assortment of applications due to its chemical resistance, relative ease of installation, durability and cost advantages, and the like. Indeed, plastic polyethylene piping has achieved significant use for water mains, gas distribution, storm and sanitary sewers, interior plumbing, electrical conduits, power and communications ducts, chilled water piping, and well casings, among others. In particular, high-density polyethylene (HDPE), which generally constitutes the largest volume of the polyolefin group of plastics used for pipe, is tough, abrasion-resistant and flexible (even at subfreezing temperatures). Furthermore, HDPE pipe may be used in small diameter tubing and in pipe up to more than 8 feet in diameter. In general, polyethylene pellets (resins) may be supplied for the pressure piping markets, such as in natural gas distribution, and for the non-pressure piping markets, such as for conduit and corrugated piping.

Rotational molding is a high-temperature, low-pressure process used to form hollow parts through the application of heat to biaxially-rotated molds. Polyethylene pellet resins generally applicable in this process are those resins that flow together in the absence of pressure when melted to form a bubble-free part. Resins, such as those produced by the catalyst compositions of the present techniques, may offer such flow characteristics, as well as a wide processing window. Furthermore, these polyethylene resins suitable for rotational molding may exhibit desirable low-temperature impact strength, good load-bearing properties, and good ultraviolet (UV) stability. Accordingly, applications for rotationally-molded polyolefin resins include agricultural tanks, industrial chemical tanks, potable water storage tanks, industrial waste containers, recreational equipment, marine products, plus many more.

Sheet extrusion is a technique for making flat plastic sheets from a variety of resins. The relatively thin gauge sheets are generally thermoformed into packaging applications such as drink cups, deli containers, produce trays, baby wipe containers and margarine tubs. Other markets for sheet extrusion of polyolefin include those that utilize relatively thicker sheets for industrial and recreational applications, such as truck bed liners, pallets, automotive dunnage, playground equipment, and boats. A third use for extruded sheet, for example, is in geomembranes, where flat-sheet polyethylene material may be welded into large containment systems for mining applications and municipal waste disposal.

The blown film process is a relatively diverse conversion system used for polyethylene. The American Society for Testing and Materials (ASTM) defines films as less than 0.254 millimeter (10 mils) in thickness. However, the blown film process can produce materials as thick as 0.5 millimeter (20 mils), and higher. Furthermore, blow molding in conjunction with monolayer and/or multilayer coextrusion technologies lays the groundwork for several applications. Advantageous properties of the blow molding products may include clarity, strength, tearability, optical properties, and toughness, to name a few. Applications may include food and retail packaging, industrial packaging, and non-packaging applications, such as agricultural films, hygiene film, and so forth.

The cast film process may differ from the blown film process through the fast quench and virtual unidirectional orientation capabilities. These characteristics allow a cast film line, for example, to operate at higher production rates while producing beneficial optics. Applications in food and retail packaging take advantage of these strengths. Finally, polyolefin pellets may also be supplied for the extrusion coating and lamination industry.

Ultimately, the products and components formed from polyolefin (e.g., polyethylene) pellets may be further processed and assembled for distribution and sale to the consumer. For example, a polyethylene milk bottle may be filled with milk for distribution to the consumer, or the fuel tank may be assembled into an automobile for distribution and sale to the consumer.

IV. Examples of Polymers Prepared Using the Catalysts of the Present Techniques

Without intending to be limiting, ethylene polymers produced using catalyst compositions of the present techniques may be characterized by lower melt elasticity than may be observed when using tightly-bridged ansa-metallocene catalysts without an alkyl group bonded to a $\eta^5$-cyclopentadienyl-type ligand. This may be demonstrated by the polymerization runs shown in Tables 1 and 2. Further, as shown in Table 1, the low steric hindrance from the linear alkyl substituent on the $\eta^5$-cyclopentadienyl-type rings may increase both activity and comonomer incorporation in some circumstances.

Figure 2:
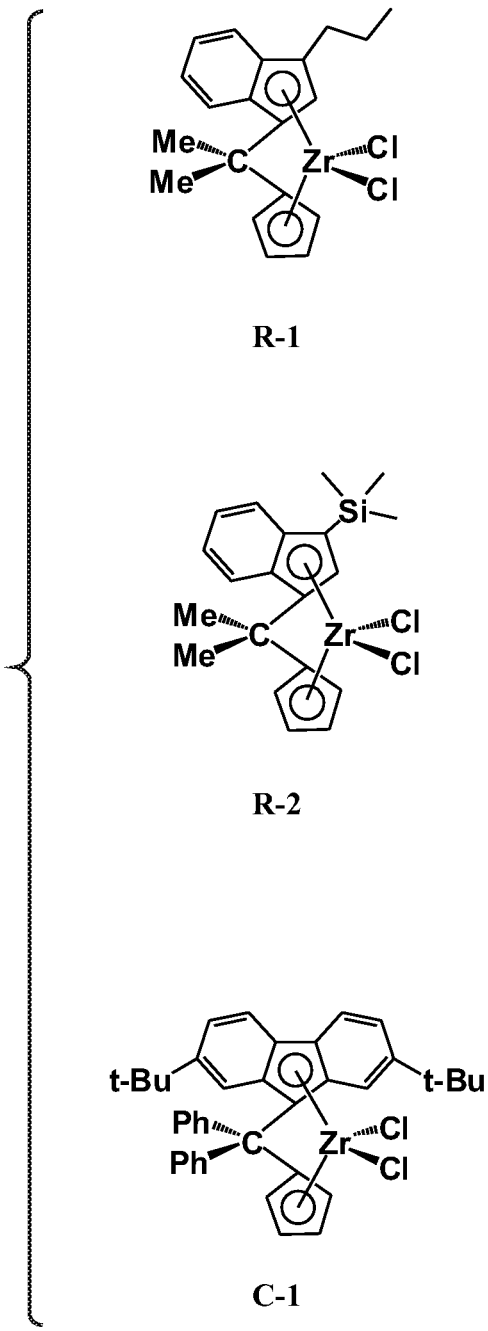
FIG. 2 represents the chemical structures of reference metallocenes.

Specifically, metallocene R-1, which has an unsubstituted alkane substituent on a $\eta^5$-indenyl ring, as shown in FIG. 2, shows higher activity, 437 g PE/mg metallocene, and higher comonomer incorporation, 0.94 mol %, than a catalyst having a bulky trimethyl silyl in the same position on the $\eta^5$-indenyl. This metallocene, shown as R-2 in FIG. 2, only has an activity of 171 g PE/mg metallocene, and a comonomer incorporation of 0.5 mol %. Thus, although the catalysts of the current techniques may be used with any of the substituents presented herein, the examples discussed below with respect to Table 2 focus on the use of unsubstituted alkyl groups as substituents.

TABLE 1

Comparison of hexene incorporation by catalysts having bulky substituents vs. linear substituents.

| Exam. | Metallocene | Metallocene Weight (mg) | Time (min) | Temp. (C.) | P (psig) | Hexene (g) | Activator-Support Type | Activator-Support (mg) | TIBAL (1M) (mL) | Solid PE (g) | Butyl Branch (mol %) |
|---|---|---|---|---|---|---|---|---|---|---|---|
| 1 | R-1 | 1 | 30 | 80 | 450 | 25.0 | Fluorided Silica Alumina | 100 | 0.5 | 437 | 0.94 |
| 2 | R-2 | 1 | 30 | 80 | 450 | 25.0 | Fluorided Silica Alumina | 100 | 0.5 | 171 | 0.50 |

Examples 3-15 in Table 2 show results that may be obtained for polymers made using the catalysts of the present techniques. The specific metallocene structures used are shown in FIG. 1, corresponding to the identification given in the column labeled "Metallocene," in Table 2. In comparison, Examples 16-18 in Table 2 show results that may be obtained for polymers made from a catalyst having no substituents on the cyclopentadienyl rings. The metallocene structure used for these runs is shown in FIG. 2 as structure "C-1." A further comparison may be made to commercially available polymers used in similar applications. Analysis results for a selection of these types of polymers are shown in Table 3.

A. Melt Elasticity

Melt elasticity may be measured by any number of rheological procedures. In one technique, as discussed below, a highly reproducible measurement of melt viscosity may be obtained from dynamic rheological measurements. The data obtained from these measurements may used to calculate a value for Tan δ, which is the ratio of the viscous modulus, G", divided by the elastic modulus, G'. As the melt elasticity decreases, G" increases and G' decreases, increasing the value of Tan δ.

Comparing the melt elasticity of different polymers may be most meaningful when the melt elasticity is correlated to the molecular weight. However, the unsubstituted metallocene catalyst, the structure of which is shown as C-1 in FIG. 2, generated a significant amount of insoluble material, preventing measurement of the molecular weights. This is indicated by the term "insolubles," in Examples 16-18. Thus, comparisons of Tan δ vs. Molecular weight, as discussed below, were impossible. As shown in Table 2, polymers made using exemplary catalysts of the present techniques, shown as I-1-I-4 in FIG. 1, all have higher values for Tan δ than the value obtained for Example 18, which was made using the unsubstituted. No such comparisons were available for Examples 16 and 17, as the melt elasticity for these samples was too high to allow for a meaningful measurement of Tan δ.

Figure 3:
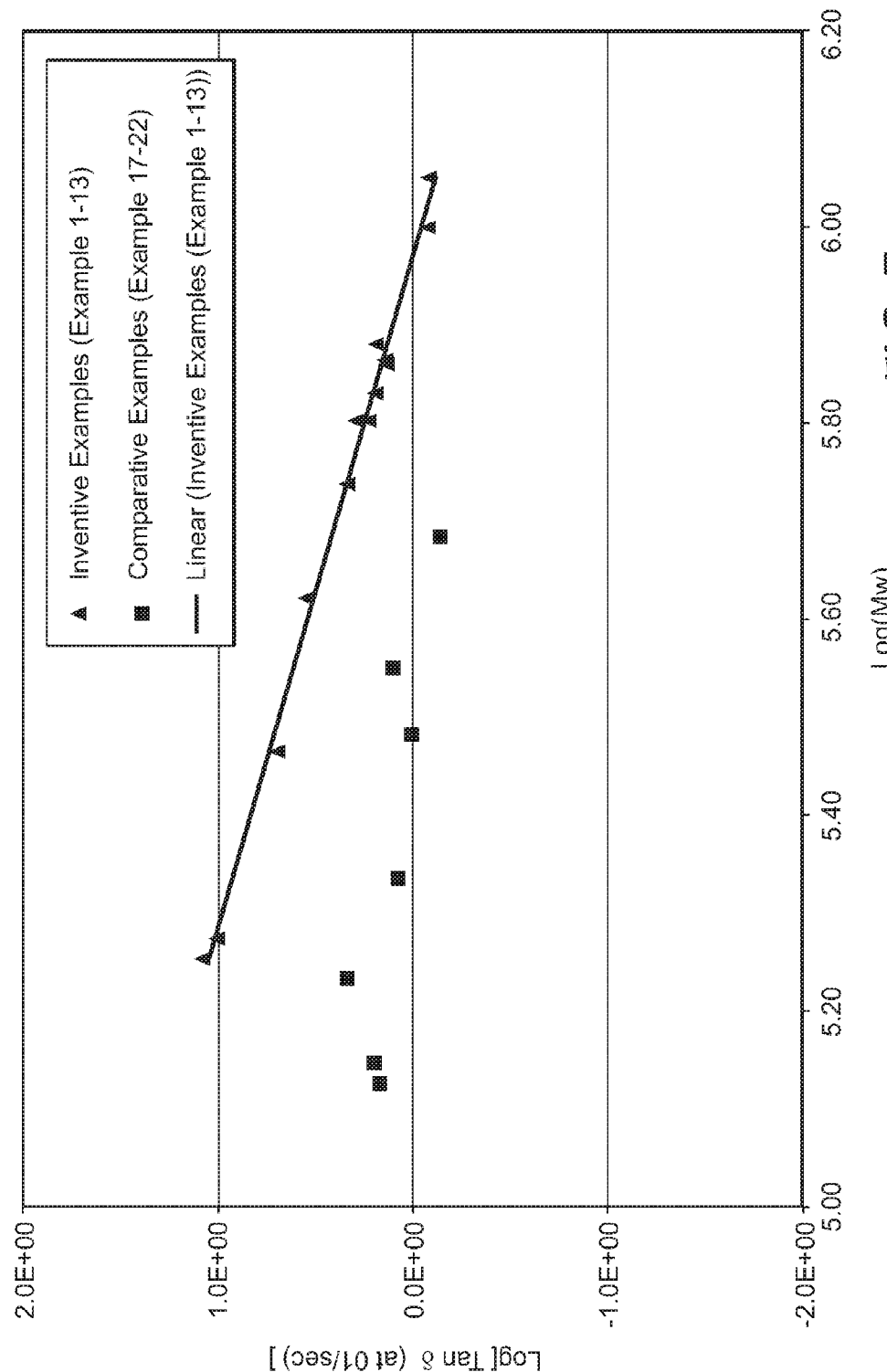
FIG. 3 represents a log-log graph of tan δ vs. molecular weight, as obtained from rheological measurements made on the exemplary ethylene homopolymers described in Examples 3-24.

Accordingly, to obtain meaningful control samples for comparisons of the melt elasticity, a variety of commercial resins were analyzed using the rheological techniques discussed above, with the results as shown in Table 3. The results obtained were plotted against molecular weight, as shown in FIG. 3. As can be seen in this log-log plot polymers produced using exemplary catalysts of the present techniques have higher values for Tan δ at comparable molecular weights to the control samples. This indicates that the melt elasticity is lower for exemplary polymers having the same molecular weight as the control polymers.

B. Results for Molecular Weight and Activity

In addition to generating polymers that may have lower melt elasticity and no insoluble components, catalysts of the present techniques may also have higher activities than unsubstituted metallocenes. As seen in Table 2, the activity of exemplary catalysts of the present techniques may range from about 1500 g P/g CTSO·hr (grams polyethylene per grams chemically treated solid oxide per hour) up to at least about 9000 g P/g CTSO·hr. By comparison, under similar conditions, the activity of an unsubstituted metallocene, shown as C-1 in FIG. 2, ranged from about 300 to about 600 g P/g CTSO·hr.

TABLE 2

Polymerization examples.

| Example | Metallocene | Time (min) | Temperature (C.) | Reactor pressure (psi) | Support Type | Support weight (mg) | R3Al (mmol) | Metallocene weight (mg) | Solid PE (g) | Mn/1000 | Mw/1000 | Mz/1000 | Mw/Mn | Tanδ (at 0.1/sec) | Activity (g P/(g CTSO·hr) |
|---|---|---|---|---|---|---|---|---|---|---|---|---|---|---|---|
| 3 | I-1 | 60 | 95 | 450 | S-SSA[1] | 100 | 0.25 TIBAL | 3.0 | 159.0 | 431.96 | 1124.28 | 2486.16 | 2.6 | 0.8173 | 1590 |
| 4 | I-1 | 60 | 95 | 450 | S-SSA | 200 | 0.25 TIBAL | 3.0 | 405.0 | 256.57 | 725.57 | 1634.92 | 2.83 | 1.3400 | 2025 |
| 5 | I-2 | 25 | 90 | 450 | S-SSA | 100 | 0.5 TNBAL | 1.0 | 295.0 | 230.42 | 547.01 | 1103.58 | 2.37 | 2.1430 | 7080 |
| 6 | I-2 | 30 | 90 | 450 | S-SSA | 100 | 0.5 TNBAL | 0.5 | 245.0 | 293.73 | 677.17 | 1288.15 | 2.31 | 1.5440 | 4900 |
| 7 | I-2 | 30 | 80 | 450 | S-SSA | 100 | 0.25 TNBAL | 1.0 | 150.0 | 409.16 | 999.82 | 2078.94 | 2.44 | 0.8280 | 3000 |
| 8 | I-2 | 30 | 90 | 390 | S-SSA | 100 | 0.5 TNBAL | 0.5 | 130.0 | 314.42 | 759.98 | 1526.1 | 2.42 | 1.5320 | 2600 |
| 9 | I-2 | 30 | 95 | 420 | S-SSA | 100 | 0.5 TNBAL | 0.5 | 161.0 | 270.4 | 635.42 | 1226.16 | 2.35 | 1.9470 | 3220 |
| 10 | I-2 | 30 | 100 | 450 | S-SSA | 100 | 0.5 TNBAL | 1.0 | 454.0 | 182.47 | 417.94 | 792.18 | 2.29 | 3.5290 | 9080 |
| 11 | I-2 | 30 | 90 | 420 | S-SSA | 100 | 0.5 TNBAL | 0.5 | 176.0 | 292.79 | 635.38 | 1128.92 | 2.17 | 1.6670 | 3520 |
| 12 | I-3 | 30 | 90 | 450 | S-SSA | 100 | 0.5 TNBAL | 0.5 | 335.0 | 76.08 | 179.1 | 357.66 | 2.35 | 11.8800 | 6700 |
| 13 | I-3 | 30 | 90 | 390 | S-SSA | 100 | 0.5 TNBAL | 0.5 | 224.0 | 85.56 | 188.11 | 352.04 | 2.2 | 10.0400 | 4480 |
| 14 | I-3 | 60 | 80 | 340 | S-SSA | 100 | 0.5 TNBAL | 0.5 | 225.0 | 94.38 | 291.56 | 603.02 | 3.09 | 4.9050 | 2250 |
| 15 | I-4 | 30 | 90 | 450 | S-SSA | 100 | 0.5 TNBAL | 1.0 | 228 | 306.72 | 732.5 | 1320.63 | 2.39 | 1.3710 | 4560 |
| 16 | C-1 | 60 | 90 | 450 | S-SSA | 100 | 0.25 TIBAL | 2.0 | 42 | insolubles | insolubles | insolubles | insolubles | — | 420 |
| 17 | C-1 | 60 | 105 | 450 | S-SSA | 100 | 0.25 TIBAL | 2.0 | 63 | insolubles | insolubles | insolubles | insolubles | — | 630 |
| 18 | C-1 | 60 | 90 | 450 | S-SSA | 200.0 | 0.5 TNBAL | 2.0 | 57 | insolubles | insolubles | insolubles | insolubles | 0.3982 | 285 |

The activity of the catalysts may also be affected by the type of substituents on the bridging substituent between the two cyclopentadienyl rings. As shown by the comparison of the activities seen for Examples 5-11, made using catalyst I-2, with Examples 12-14 using catalyst I-3, phenyl rings on the bridging substituent may decrease the activity.

TABLE 3

Analysis Results for Commercial PE resins made from Cr catalysts.

| Example | Mn/1000 | Mw/1000 | Mz/1000 | Mw/Mn | Tanδ (at 0.1/sec) |
|---|---|---|---|---|---|
| 19 | 19.18 | 134.92 | 775.76 | 7.03 | 1.6130 |
| 20 | 18.17 | 140.57 | 927.05 | 7.74 | 1.5840 |
| 21 | 21.65 | 133.61 | 751.41 | 6.17 | 1.4890 |
| 22 | 21.2 | 216.41 | 2086.1 | 10.21 | 1.1980 |
| 23 | 14.62 | 354.38 | 3536.4 | 24.24 | 1.2740 |
| 24 | 14.03 | 303.53 | 2261.36 | 21.63 | 1.0330 |

V. Procedures

A. Molecular Weight Determination

Molecular weight and molecular weight distributions were obtained using a PL-GPC 220 (Polymer Labs, UK) system equipped with a differential refractive index detector and three 7.5 mm×300 mm 20 um Mixed A-LS columns (Polymer Labs) running at 145° C. The flow rate of the mobile phase, 1,2,4-trichlorobenzene (TCB) containing 0.5 g/L 2,6-di-t-butyl-4-methylphenol (BHT), was set at 1 mL/min and the concentration of polymer solutions was generally kept in the range of 1.0-1.5 mg/mL, depending on the molecular weights. Sample preparation was conducted at 150° C. for 4 h with occasional and gentle agitation before the solutions being transferred to sample vials for injection. In order to minimize unbalanced solvent peak, solvent with the same composition as the mobile phase was used for solution preparation. The integral calibration method was used to deduce molecular weights and molecular weight distributions using a Chevron Phillips Chemicals Company's linear polyethylene, Marlex BHB5003, as the broad standard. The integral table of the broad standard was pre-determined in a separate experiment with SEC-MALS.

B. Absolute Molecular Weight as Determined by SEC-MALS

Absolute molecular weight data were determined using SEC-MALS, which combines the methods of size exclusion chromatography (SEC) with multi-angle light scattering (MALS) detection. A DAWN EOS 18-angle light scattering photometer (Wyatt Technology, Santa Barbara, Calif.) was attached to a PL-210 SEC system (Polymer Labs, UK) or a Waters 150 CV Plus system (Milford, Mass.) through a hot transfer line, thermally controlled at the same temperature as the SEC columns and its differential refractive index (DRI) detector (145° C.). At a flow rate setting of 0.7 mL/min, the mobile phase, 1,2,4-trichlorobenzene (TCB), was eluted through three, 7.5 mm×300 mm, 20 μm Mixed A-LS columns (Polymer Labs). Polyethylene (PE) solutions with concentrations of ~1.2 mg/mL, depending on samples, were prepared at 150° C. for 4 h before being transferred to the SEC injection vials sitting in a carousel heated at 145° C. For polymers of higher molecular weight, longer heating times were necessary in order to obtain true homogeneous solutions. In addition to acquiring a concentration chromatogram, seventeen light-scattering chromatograms at different angles were also acquired for each injection using Wyatt's Astra® software. At each chromatographic slice, both the absolute molecular weight (M) and root mean square (RMS) radius, also known as radius of gyration ($R_g$) were obtained from a Debye plot's intercept and slope, respectively. Methods for this process are detailed in Wyatt, P. J., *Anal. Chim. Acta*, 272, 1 (1993), which is hereby incorporated herein by reference in its entirety. The linear PE control employed was a linear, high-density broad molecular weight distribution (MWD) polyethylene sample (Chevron Phillips Chemical Co.). The weight average molecular weight ($M_w$), number average molecular weight ($M_n$), z-average molecular weight ($M_z$) and molecular weight distribution ($M_w/M_n$) were computed from these data, and were used to build an integral table as a control for the relative molecular weight determination discussed above.

C. Pore Size Determination

A Quantachrome Autosorb-6 Nitrogen Pore Size Distribution Instrument was used to determine specific surface area ("surface area") and specific pore volume ("pore volume"). This instrument was acquired from the Quantachrome Corporation, Syosset, N.Y.

D. Measurement of Tan δ by Rheology

Small-strain oscillatory shear measurements were performed on an ARES oscillatory rheometer using parallel-plate geometry (TA Instruments, formerly Rheometrics Inc.). Data were typically obtained over an angular frequency range of 0.03 to 100 rad/s at a temperature of 190° C.

Fluff samples were stabilized with 0.1 wt % BHT dispersed in acetone and then vacuum dried before molding. Samples were compression molded at 184° C. for a total of three minutes. The samples were allowed to melt at a relatively low pressure for one minute and then subjected to a high molding pressure for an additional two minutes. The molded samples were then quenched in a cold (room temperature) press. Disks having the size 2 mm×25.4 mm diameter were stamped out of the molded slabs for rheological characterization.

The test chamber of the rheometer was blanketed in nitrogen in order to minimize polymer degradation. The rheometer was preheated to the initial temperature of the study. Upon sample loading and after oven thermal equilibration, the specimens were squeezed between the plates to a 1.6 mm thickness and the excess was trimmed.

Strains were generally maintained at a single value throughout a frequency sweep but larger strain values were used for low viscosity samples to maintain a measurable torque. Smaller strain values were used for high viscosity samples to avoid overloading the torque transducer and to keep within the linear viscoelastic limits of the sample. The instrument automatically reduces the strain at high frequencies if necessary to keep from overloading the torque transducer. Tan δ was calculated from the rheological measurements as the ratio of the viscous modulus, G", divided by the elastic modulus, G'.

E. Preparation of a Fluorided Silica-Alumina Activator-Support

The silica-alumina used to prepare the fluorided silica-alumina acidic activator-support in this Example was typically Davison silica-alumina obtained from W.R. Grace as Grade MS13-110, containing 13% alumina, having a pore volume of about 1.2 cc/g and a surface area of about 400 m²/g. This material was fluorided by impregnation to incipient wetness with a solution containing ammonium bifluoride in an amount sufficient to equal 10 wt % of the weight of the silica-alumina. This impregnated material was then dried in a vacuum oven for 8 hours at 100° C. The fluorided silica-alumina samples were then calcined. Calcination was performed by placing about 10 grams of the alumina in a 1.75-inch quartz tube fitted with a sintered quartz disk at the bottom. While the silica was supported on the disk, dry air was blown up through the disk at the linear rate of about 1.6 to 1.8 standard cubic feet per hour. An electric furnace around the quartz tube was employed to increase the temperature of the tube at the rate of about 400° C. per hour to a final temperature of about 500° C. At this temperature, the silica-alumina was allowed to fluidize for about three hours in the dry air. Afterward, the silica-alumina was collected and stored under dry nitrogen, and was used without exposure to the atmosphere.

F. Preparation of a Sulfated Alumina Activator-Support

Sulfated alumina was formed by a process wherein alumina was chemically-treated with a sulfate or bisulfate source. Such a sulfate or bisulfate source may include, for example, sulfuric acid, ammonium sulfate, or ammonium bisulfate.

In an exemplary procedure, a commercial alumina sold as W.R. Grace Alumina A was sulfated by impregnation with an aqueous solution containing about 15-20% $(NH_4)_2SO_4$ or $H_2SO_4$. This sulfated alumina was calcined at 550° C. in air (240° C./h ramp rate), with a 3 h hold period at this temperature. Afterward, the alumina was collected and stored under dry nitrogen, and was used without exposure to the atmosphere.

G. Procedures for Metallocene and Polymer Synthesis

Compounds In-1, In-2, L-5, L-6, R-1 and R-2 were prepared following the procedure disclosed in U.S. Pat. No. 7,026,494, which is incorporated by reference in its entirety herein. Preparation procedures for the fulvenes whose chemical structures are shown below are presented in the following subsections: 1 (F-1), 2 (F-2), 3 (F-3), and 4 (F-4).

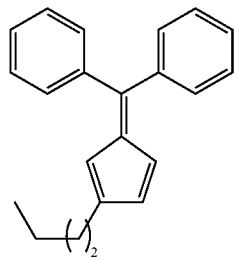

F-1

2-(butyl)-6,6-diphenylpentafulvene

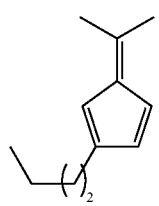

F-2

2-(butyl)-6,6-dimethylpentafulvene

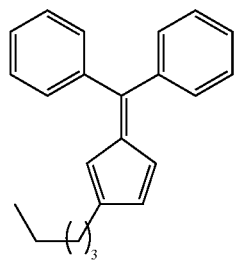

F-3

2-(pentyl)-6,6-diphenylpentafulvene

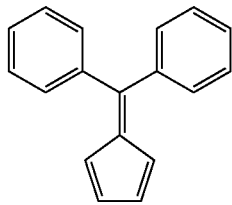

F-4

6,6-diphenylpentafulvene

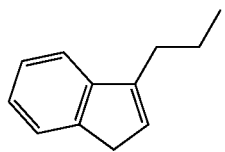

In-1

3-propyl-1H-indene

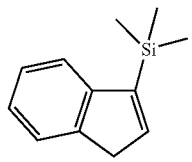

In-2

3-(trimethylsilyl)-1H-indene

After preparation, these fulvenes were used to prepare the ligands whose chemical structures are listed below, as presented in the following subsections: 5 (L-1), 6 (L-2), 7 (L-3), and 8 (L-4).

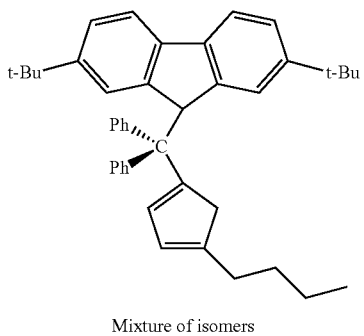

L-1

Mixture of isomers

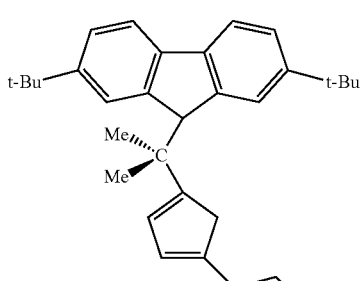

L-2

Mixture of isomers

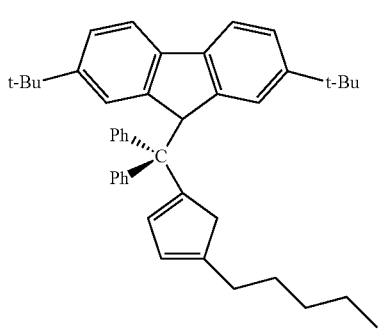

L-3

Mixture of isomers

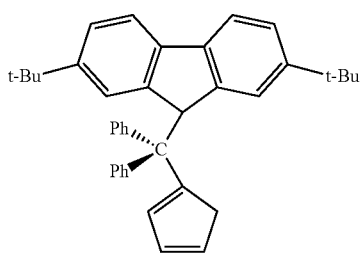

L-4

Mixture of isomers

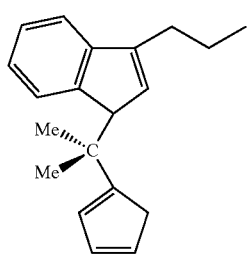

L-5

Mixture of isomers

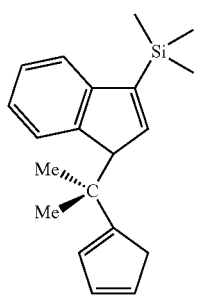

L-6

Mixture of isomers

Procedures using ligands L-1, L-2, L-3, and L-4 to prepare the exemplary metallocenes are presented in the following subsections: 9 (I-1), 10 (I-2), 11 (I-3), and 12 (I-4). A procedure for preparing the comparative metallocene, C-1, is presented in subsection 13. Subsection 14 discloses the source of the comparative commercial polyethylene samples. Subsection 15 discloses exemplary procedures for preparing polymers using the catalyst compositions of the present techniques.

Unless specified otherwise, reagents were obtained from Aldrich Chemical Company and were used as received. 2,7-Di-tert-butylfluorene was purchased from Degussa. The Grignard reagent CpMgCl (1M in THF) was purchased from Boulder Scientific Company. Hafnium(IV) chloride and zirconium(IV) chloride were purchased from Strem. The solvent tetrahydrofuran (THF) was distilled from potassium, while anhydrous diethyl ether, dichloromethane, n-pentane, and toluene were purchased from Fisher Scientific Company and stored over activated alumina. All solvents were degassed and stored under nitrogen. Reported preparations were not optimized.

1. Synthesis of 2-butyl-6,6-diphenylpentafulvene (F-1)

To 1-bromobutane (34.2 g of 99 wt %, 0.247 mol) was added cyclopentadienyl magnesium chloride (260 mL of 1 M solution in THF, 0.26 mol) at 0° C. in 25 minutes. After stirring for an additional 15 minutes at 0° C., the mixture was warmed to room temperature. After stirring overnight, the reaction was quenched with a mixture of ice and water. The mixture was extracted with pentane. The organic layer was washed with water and dried over anhydrous sodium sulfate. Removal of the solvent under vacuum at room temperature gave a yellow liquid (30.5 g, crude butylcyclopentadiene). To the crude butylcyclopentadiene (20.5 g) dissolved in THF (150 mL) was added n-BuLi (15 mL of 10 M in hexanes, 0.15 mol) at −78° C. The mixture was warmed up to room temperature and stirred for 5 hours. The anion solution was added to benzophenone (28 g, 0.154 mol) dissolved in THF (100 mL) at 0° C. in 13 minutes. The mixture was warmed to room temperature and stirred overnight. The reaction was quenched with a mixture of ice and 10% HCl aqueous solution. The mixture was extracted with pentane. The organic layer was washed with water and dried over anhydrous sodium sulfate. Removal of the solvent under vacuum at 40° C. gave a dark red viscous oil. The oil was dissolved in heptane and filtered through silica gel. The product was collected by washing the silica gel with 5-10% $CH_2Cl_2$ in heptane. Removal of the solvent gave the desired product (22.3 g, 47% yield based on 1-bromobutane) as a dark red viscous oil.

2. Synthesis of 2-butyl-6,6-dimethylpentafulvene (F-2)

To 1-bromobutane (105 g, 0.766 mol) was added cyclopentadienyl magnesium chloride (800 mL of 1 M solution in THF, 0.8 mol) at 0° C. in 20 minutes. After stirring for an additional 2 hours at 0° C., the mixture was warmed to room temperature. After stirring overnight, the reaction was quenched with a mixture of ice and water. The mixture was extracted with pentane. The organic layer was washed with water and dried over anhydrous sodium sulfate. Removal of the solvent under vacuum at room temperature gave a brown liquid (85 g, crude butylcyclopentadiene). To the crude butylcyclopentadiene (75 g) dissolved in methanol (500 mL) was added acetone (54 mL) followed by pyrrolidine (63 mL) at 0° C. The mixture was warmed up to room temperature and stirred for 24 hours. The reaction was quenched with a mixture of ice and acetic acid. The mixture was extracted with pentane. The organic layer was washed with water and dried over anhydrous sodium sulfate. Removal of the solvent under vacuum gave the desired product (89 g) as a brown liquid.

3. Synthesis of 2-pentyl-6,6-diphenylpentafulvene (F-3)

To 1-bromopentane (109.8 g, 0.727 mol) was added cyclopentadienyl magnesium chloride (800 mL of 1 M solution in THF, 0.8 mol) at 0° C. in 15 minutes. After stirring for an additional 2 hours at 0° C., the mixture was warmed to room temperature. After stirring overnight, the reaction was quenched with a mixture of ice and water. The mixture was extracted with pentane. The organic layer was washed with water and dried over anhydrous sodium sulfate. Removal of the solvent under vacuum at room temperature gave a brown liquid (101.4 g, crude pentylcyclopentadiene). To the crude pentylcyclopentadiene (50 g) dissolved in THF (200 mL) was added n-BuLi (35 mL of 10 M in hexanes, 0.35 mol) at 0° C. The mixture was warmed up to room temperature and stirred overnight. The anion solution was added to benzophenone (60.7 g, 0.334 mol) dissolved in THF (280 mL) at 0° C. in 25 minutes. The mixture was warmed to room temperature and stirred overnight. The reaction was quenched with a mixture of ice and 10% HCl aqueous solution. The mixture was extracted with pentane. The organic layer was washed with water and dried over anhydrous sodium sulfate. Removal of the solvent under vacuum at 50° C. gave a dark red viscous oil. The oil was dissolved in heptane and filtered through silica gel. The product was collected by washing the silica gel with 5-10% $CH_2Cl_2$ in heptane. Removal of the solvent gave the desired product (74.3 g) as a dark red viscous oil.

4. Synthesis of 6,6-diphenylpentafulvene (F-4)

Benzophenone (63.8 g, 350 mmol) was dissolved in anhydrous 1,2-dimethoxyethane (DME) (150 mL) under nitrogen. In a one-liter flask, ground potassium hydroxide (30 g, 535 mmol) was slurried in DME (200 mL). The slurry was cooled in an ice bath and freshly cracked cyclopentadiene (35 mL, 430 mmol) was added. After 30 minutes, the solution of benzophenone was added over 15 minutes. The flask was stirred in a refrigerator for 90 hours and then, while cooling in ice, 3M HCl (450 mL) was added. The mixture was diluted with pentane (500 mL) and separated. The organic layer was washed with water (2×200 mL) and dried over sodium sulfate. The solution was filtered and taken to dryness under vacuum. The solid was dissolved in boiling pentane (600 mL) and then concentrated to 400 mL. Cooling to −15° C. for 40 hours gave a red solid (69.5 g, 86.3% yield). (F-4 may also be commercially available from Sigma-Aldrich).

5. Synthesis of 1-(3-butylcyclopentadien-1-yl)-1-(2,7-di-tert-butylfluoren-9-yl)-1,1-diphenylmethane (L-1)

To 2,7-di-tert-butylfluorene (15 g, 54 mmol) dissolved in $Et_2O$ (100 mL) was added n-BuLi (5.8 mL of 10 M in hexanes, 58 mmol) at 0° C. The mixture was warmed to room temperature and stirred overnight. The anion solution was added to 2-butyl-6,6-diphenylpentafulvene (F-1) (16 g, 56 mmol) dissolved in $Et_2O$ (100 mL) at −78° C. in 5 minutes. The mixture was warmed to room temperature and stirred for 2 days. The reaction was quenched with a mixture of ice and 10% HCl aqueous solution. The mixture was extracted with $Et_2O$. The organic layer was washed with water and dried over anhydrous sodium sulfate. Removal of the solvent under vacuum gave a viscous oil. The oil was stirred in heptane to give a white solid. The solid was filtered, washed with heptane and dried under vacuum. A mixture of isomers for the desired product (18.7 g, 61.3% yield) was obtained as a white solid.

6. Synthesis of 1-(3-butylcyclopentadien-1-yl)-1-(2,7-di-tert-butylfluoren-9-yl)-1,1-dimethylmethane (L-2)

To 2,7-di-tert-butylfluorene (27.8 g, 100 mmol) dissolved in $Et_2O$ (200 mL) was added n-BuLi (11 mL of 10 M in hexanes, 110 mmol) at 0° C. The mixture was warmed to room temperature and stirred overnight. To the anion solution was added to 2-butyl-6,6-dimethylpentafulvene (F-2) (20 g, 123 mmol) at −78° C. in less than one minute. The mixture was warmed to room temperature and stirred overnight. The reaction was quenched with a mixture of ice and saturated $NH_4Cl$ aqueous solution. The mixture was extracted with $Et_2O$. The organic layer was washed with water and dried over anhydrous sodium sulfate. Removal of the solvent under vacuum gave a viscous oil. The oil was dissolved in heptane and purified through silica gel column with 5-10% $CH_2Cl_2$ in heptane. A mixture of isomers for the desired product (33.8 g, 76.8% yield) was obtained as a viscous oil.

7. Synthesis of 1-(3-pentylcyclopentadien-1-yl)-1-(2,7-di-tert-butylfluoren-9-yl)-1,1-diphenylmethane (L-3)

To 2,7-di-tert-butylfluorene (18 g, 64.7 mmol) dissolved in $Et_2O$ (100 mL) was added n-BuLi (6.8 mL of 10 M in hexanes, 68 mmol) at 0° C. The mixture was warmed to room temperature and stirred overnight. The anion solution was added to 2-pentyl-6,6-diphenylpentafulvene (F-3) (20 g, 67 mmol) dissolved in $Et_2O$ (100 mL) at −78° C. in 2 minutes. The mixture was warmed to room temperature and stirred for 2 days. The reaction was quenched with a mixture of ice and 10% HCl aqueous solution. The mixture was extracted with $Et_2O$. The organic layer was washed with water and dried over anhydrous sodium sulfate. Removal of the solvent under vacuum gave a viscous oil. The oil was stirred in heptane to give a white solid. The solid was filtered, washed with heptane and dried under vacuum. A mixture of isomers for the desired product (22.7 g, 60.7% yield) was obtained as a white solid.

8. Synthesis of 1-(cyclopentadien-1-yl)-1-(2,7-di-tert-butylfluoren-9-yl)-1,1-diphenylmethane (L-4)

To a solution of 2,7-di-tert-butylfluorene (29.8 g, 107 mmol) in dry tetrahydrofuran (THF) (100 mL), cooled in dry ice, was added n-BuLi (43.0 mL of 2.5 M in hexanes, 107.5 mmol). The bath was removed and the dark solution was stirred for 2 hours. This solution was then added dropwise to a solution of 6,6-diphenylpentafulvene (F-4) (26.0 g, 113 mmol) in THF (100 mL), while cooling in ice. The reaction mixture was stirred at room temperature for 86 hours and then cooled in ice. 1M HCl solution, (100 mL) was added. The mixture was diluted with chloroform (100 mL) and separated. The chloroform layer was washed with water (3×100 mL) and dried over sodium sulfate. The solution was filtered and evaporated to a light orange solid. The solid was dissolved in boiling chloroform (150 mL) and methanol (150 mL) was slowly added. After cooling for two days to −15° C., the solid was filtered off, ground, and dried under vacuum. The desired product (25.4 g, 46.7% yield) was obtained as an off white solid.

9. Synthesis of [1-($\eta^5$-3-butylcyclopentadien-1-yl)-1-($\eta^5$-2,7-di-tert-butylfluoren-9-yl)-1,1-diphenylmethane]hafnium dichloride(I-1 in FIG. 1).

To 1-(3-butylcyclopentadienyl)-1-(2,7-di-tert-butylfluorenyl)-1,1-diphenylmethane (L-1) (6.7 g, 11.9 mmol) dissolved in $Et_2O$ (60 mL) was slowly added n-BuLi (2.6 mL of 10 M in hexanes, 26 mmol) at 0° C. The mixture was warmed to room temperature, stirred overnight, and then added via cannula to $HfCl_4$ (4.2 g, 13 mmol) suspended in a mixture of pentane (60 mL) and Et$_2$O (10 mL) at 0° C. The mixture was warmed to room temperature, stirred overnight, and evacuated to dryness. The residue was stirred in pentane (50 mL) and centrifuged. The supernatant was discarded. The remaining solid was washed a second time with pentane (30 mL), then extracted with methylene chloride and centrifuged. The solution was taken to dryness under vacuum to give a yellow solid (6.7 g, 69.4% yield).

10. Synthesis of [1-($\eta^5$-3-butylcyclopentadien-1-yl)-1-($\eta^5$-2,7-di-tert-butylfluoren-9-yl)-1,1-diphenylmethane]zirconium dichloride (I-2 in FIG. 1).

To 1-(3-butylcyclopentadienyl)-1-(2,7-di-tert-butylfluorenyl)-1,1-diphenylmethane (L-1) (7.9 g, 14 mmol) dissolved in Et$_2$O (70 mL) was slowly added n-BuLi (3 ml, of 10 M in hexanes, 30 mmol) at 0° C. The mixture was warmed to room temperature, stirred overnight, and then added via cannula to ZrCl$_4$ (3.43 g, 14.7 mmol) suspended in a mixture of pentane (70 mL) and Et$_2$O (10 mL) at 0° C. The mixture was warmed to room temperature, stirred overnight, and evacuated to dryness. The residue was stirred in pentane (100 mL) and centrifuged. The supernatant was discarded. The remaining solid was washed a second time with pentane (50 mL), then extracted with methylene chloride and centrifuged. The solution was taken to dryness under vacuum to give an orange solid (7 g, 69.3% yield).

11. Synthesis of [1-($\eta^5$-3-butylcyclopentadien-1-yl)-1-($\eta^5$-2,7-di-tert-butylfluoren-9-yl)-1,1-dimethylmethane]zirconium dichloride (I-3 in FIG. 1).

To 1-(3-butylcyclopentadienyl)-1-(2,7-di-tert-butylfluorenyl)-1,1-dimethylmethane (L-2) (12 g, 27.3 mmol) dissolved in Et$_2$O (150 mL) was slowly added n-BuLi (6 mL of 10 M in hexanes, 60 mmol) at 0° C. The mixture was warmed to room temperature, stirred overnight, and then added via cannula to ZrCl$_4$ (7 g, 30 mmol) suspended in a mixture of pentane (150 mL) and Et$_2$O (10 mL) at 0° C. The mixture was warmed to room temperature, stirred overnight, and evacuated to dryness. The residue was stirred in pentane (100 mL) and centrifuged. The supernatant was discarded. The remaining solid was washed a second time with pentane (100 mL), then extracted with methylene chloride and centrifuged. The solution was taken to dryness under vacuum to give a red solid (11.8 g, 72% yield).

12. Synthesis of [1-($\eta^5$-3-pentylcyclopentadien-1-yl)-1-($\eta^5$-2,7-di-tert-butylfluoren-9-yl)-1,1-diphenylmethane]zirconium dichloride (I-4 in FIG. 1).

To 1-(3-pentylcyclopentadienyl)-1-(2,7-di-tert-butylfluorenyl)-1,1-diphenylmethane (L-3) (8 g, 13.8 mmol) dissolved in Et$_2$O (70 mL) was slowly added n-BuLi (3 ml, of 10 M in hexanes, 30 mmol) at 0° C. The mixture was warmed to room temperature, stirred overnight, and then added via cannula to ZrCl$_4$ (3.4 g, 14.7 mmol) suspended in a mixture of pentane (70 mL) and Et$_2$O (10 mL) at 0° C. The mixture was warmed to room temperature, stirred overnight, and evacuated to dryness. The residue was stirred in pentane (50 mL) and centrifuged. The supernatant was discarded. The remaining solid was washed a second time with pentane (50 mL), then extracted with methylene chloride and centrifuged. The solution was taken to dryness under vacuum to give an orange solid (6.9 g, 73.5% yield).

13. Synthesis of [1-($\eta^5$-cyclopentadien-1-yl)-1-($\eta^5$-2,7-di-tert-butylfluoren-9-yl)-1,1-diphenylmethane]zirconium dichloride (C-1 in FIG. 2).

Under nitrogen, 1-cyclopentadienyl-1-(2,7-di-tert-butylfluorenyl)-1,1-diphenylmethane (L-4) (15.26 g, 30.0 mmol) was suspended in dry Et$_2$O (250 mL). While cooling in dry ice, n-BuLi (24.0 mL of 2.5 M in hexanes, 60 mmol) were added dropwise. The bath was then removed and the mixture was stirred for 24 hours. The solution was gradually added to zirconium tetrachloride (7.38 g, 31.7 mmol) suspended in pentane (50 mL) and cooled in ice. The orange slurry was stirred for 90 hours and allowed to warm to room temperature. The resulting slurry was centrifuged and the solid was mixed with dry methylene chloride (120 mL). The mixture was centrifuged and the solution was removed and taken to dryness under vacuum. The desired product (9.63 g, 48% yield) was obtained as an orange solid.

14. Commercial Polyethylene Samples

Commercial polyethylene resins, as shown in Examples 19-24 in Table 3, were analyzed to determine Tan δ and molecular weight properties for comparison to Examples 3-15 given in Table 2. These resins were prepared using commercial chromium catalyst systems. All of the resins tested are available from Chevron Phillips Chemical Company under the product numbers shown in the column entitled "Commercial Resin."

15. Polymerization Procedures for Examples 1-18

Examples 1-18 in Tables 1 and 2 illustrate ethylene polymerization runs performed in a one-gallon (3.785 liter) stainless steel autoclave reactor at various temperatures, using two liters of isobutane diluent and an aluminum alkyl cocatalyst and scavenger. No hydrogen or comonomer was added. Metallocene solutions (2 mg/mL) were typically prepared by dissolving 30 mg of the metallocene in 15 mL of toluene. A typical polymerization procedure is as follows. The aluminum alkyl compound, treated solid oxide, and the metallocene solution were added through a charge port, typically in that order, while venting isobutane vapor. The charge port was closed and two liters of isobutane were added. The contents of the reactor were stirred and heated to the desired run temperature. Ethylene was fed on demand to maintain the specified pressure for the specified length of the polymerization run. The reactor was maintained at the desired run temperature through the run by an automated heating and cooling system.

After the allotted polymerization time, the ethylene flow was stopped, and the reactor slowly depressurized and opened to recover a granular polymer. In all cases, the reactor was clean with no indication of any wall scale, coating or other forms of fouling. The polymer was then removed and weighed, giving the results listed in Tables 1 and 2, above.

While the techniques presented herein may be susceptible to various modifications and alternative forms, specific embodiments have been shown by way of example in the drawings and have been described in detail herein. However, it should be understood that the invention is not intended to be limited to the particular forms presented. Rather, the invention is to cover all modifications, equivalents and alternatives falling within the spirit and scope of the invention as defined by the following appended claims.

What is claimed is:

1. A method of polymerizing olefins, comprising:

contacting an α-olefin with a catalyst composition under polymerization conditions to form a polymer;

wherein the catalyst composition comprises the contact product of an ansa-metallocene, an organoaluminum compound, and an activator, wherein:

the ansa-metallocene comprises a compound having the formula:

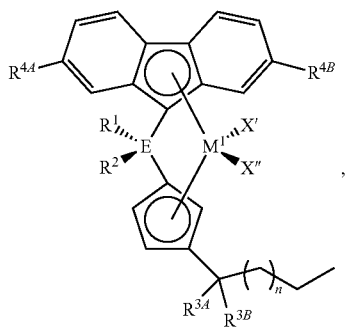

wherein:

$M^1$ is zirconium or hafnium;

X' and X" are independently F, Cl, Br, or I;

E is C or Si;

$R^1$ and $R^2$ are independently an alkyl group, an aryl group, or hydrogen;

$R^{3A}$ and $R^{3B}$ are independently a hydrocarbyl group, a trihydrocarbylsilyl group, or hydrogen;

n is an integer from 0 to 10, inclusive;

$R^{4A}$ and $R^{4B}$ are independently a hydrocarbyl group; and the activator comprises an activator-support comprising a solid oxide treated with an electron-withdrawing anion.

2. The method of claim 1, wherein the organoaluminum compound has the formula:

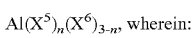

$X^5$ is a hydrocarbyl;

$X^6$ is a halide, a hydride, an alkoxide or an aryloxide; and n is a number from 1 to 3, inclusive.

3. The method of claim 2, wherein:

the ansa-metallocene comprises:

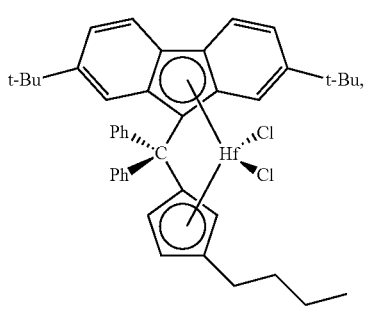

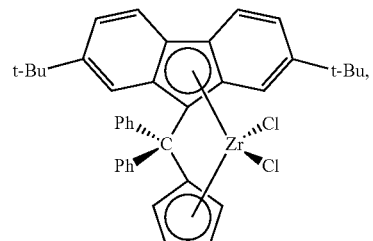

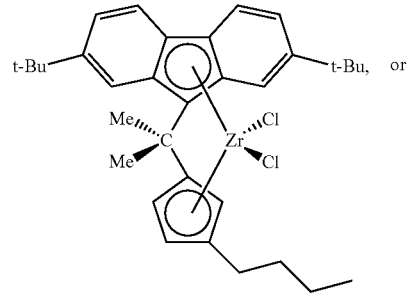

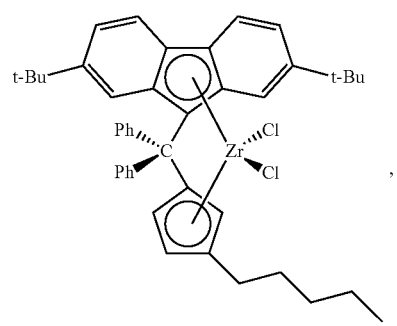

or any combination thereof the activator comprises a sulfated solid oxide; and the organoaluminum compound comprises triethylaluminum, tri-n-butylaluminum, triisobutylaluminum, or any combination thereof.

4. The method of claim 2, wherein:

the ansa-metallocene comprises:

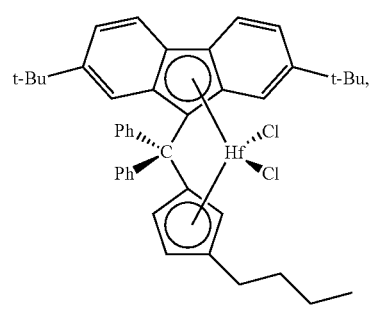

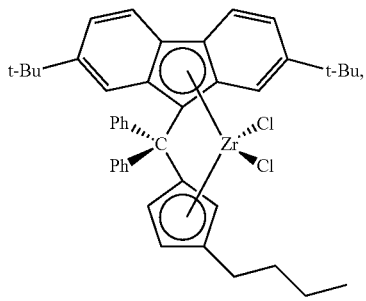

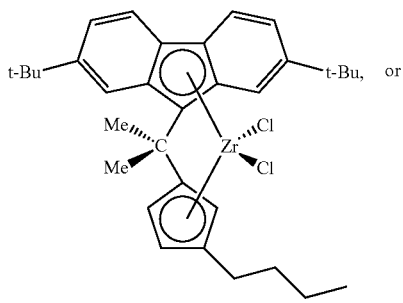

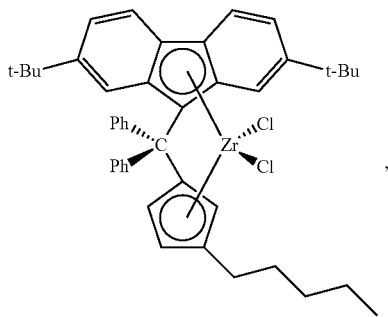

or any combination thereof;

the activator comprises sulfated alumina; and the organoaluminum compound comprises triethylaluminum, tri-n-butylaluminum, triisobutylaluminum, or any combination thereof.

5. The method of claim 1, wherein the activator comprises an organoboron compound, an organoborate compound, an organoaluminoxane compound, or any combination thereof, wherein the organoaluminoxane compound comprises:

a cyclic aluminoxane having the formula:

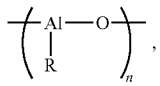

wherein R is a linear or branched alkyl and n is an integer from 3 to about 10;

a linear aluminoxane having the formula:

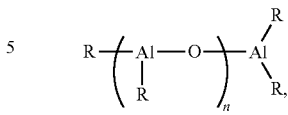

wherein R is a linear or branched alkyl and n is an integer from 1 to about 50; or a cage aluminoxane having the formula $R^t_{5m+\alpha} R^b_{m-\alpha} Al_{4m} O_{3m}$, wherein:

m is 3 or 4;

α is equal to $n_{Al(3)} - n_{O(2)} + n_{O(4)}$, wherein:

$n_{Al(3)}$ is the number of three coordinate aluminum atoms;

$n_{O(2)}$ is the number of two coordinate oxygen atoms; and $n_{O(4)}$ is the number of four coordinate oxygen atoms;

$R^t$ represents a linear or branched terminal alkyl group; and $R^b$ represents a linear or branched bridging alkyl group; or any combination thereof.

6. The method of claim 1, wherein:

the solid oxide is silica, alumina, silica-alumina, aluminophosphate, aluminum phosphate, zinc aluminate, heteropolytungstates, titania, zirconia, magnesia, boria, zinc oxide, mixed oxides thereof, or any combination thereof; and the electron-withdrawing anion is fluoride, chloride, bromide, iodide, phosphate, triflate, bisulfate, sulfate, fluoroborate, fluorosulfate, trifluoroacetate, phosphate, fluorophosphate, fluorozirconate, fluorosilicate, fluorotitanate, permanganate, substituted or unsubstituted alkanesulfonate, substituted or unsubstituted arenesulfonate, substituted or unsubstituted alkylsulfate, or any combination thereof.

7. The method of claim 1, wherein $R^{3A}$ and $R^{3B}$ are independently H, methyl, allyl, ethyl, propyl, benzyl, butyl, pentyl, hexyl, or trimethylsilyl.

8. The method of claim 1, wherein the α-olefin is contacted with the catalyst composition in a reactor system comprising a batch reactor, a slurry reactor, a gas-phase reactor, a solution reactor, a high pressure reactor, a tubular reactor, an autoclave reactor, or any combination thereof.

9. The method of claim 8, wherein the reactor system comprises the slurry reactor, the slurry reactor comprises a loop slurry reactor, and the polymer formed is continuously removed from the reactor.

10. The method of claim 1, wherein the organoaluminum compound is a trialkylaluminum compound.

11. The method of claim 1, wherein the α-olefin comprises a monomer, or a monomer and a comonomer.

12. The method of claim 11, wherein the monomer comprises ethylene, propylene, or a combination thereof.

13. The method of claim 11, wherein the α-olefin comprises the monomer and the comonomer, and the comonomer comprises propylene, 1-butene, 1-pentene, 1-hexene, 1-heptene, or 1-octene, or any combination thereof.

14. A method of polymerizing olefins, comprising:

contacting an α-olefin with a catalyst composition under polymerization conditions to form a polymer;

wherein the catalyst composition comprises the contact product of an ansa-metallocene and an activator, wherein:

the ansa-metallocene comprises a compound having the formula:

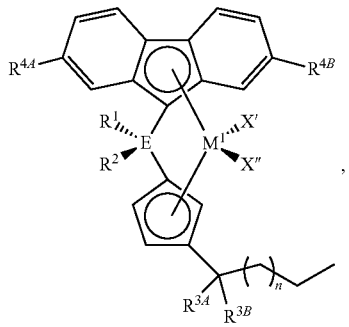

wherein:
M¹ is zirconium or hafnium;
X' and X" are independently H, BH$_4$, methyl, phenyl, benzyl, neopentyl, trimethylsilylmethyl, CH$_2$CMe$_2$Ph, CH$_2$SiMe$_2$Ph, CH$_2$CMe$_2$CH$_2$Ph, or CH$_2$SiMe$_2$CH$_2$Ph;
E is C or Si;
R¹ and R² are independently an alkyl group, an aryl group, or hydrogen;
R$^{3A}$ and R$^{3B}$ are independently a hydrocarbyl group, a trihydrocarbylsilyl group, or hydrogen;
n is an integer from 0 to 10, inclusive;
R$^{4A}$ and R$^{4B}$ are independently a hydrocarbyl group; and
the activator comprises an activator-support comprising a solid oxide treated with an electron-withdrawing anion.

15. The method of claim 14, wherein the solid oxide of the activator-support is silica, alumina, silica-alumina, aluminophosphate, aluminum phosphate, zinc aluminate, heteropolytungstates, titania, zirconia, magnesia, boria, zinc oxide, mixed oxides thereof, or any combination thereof; and
the electron-withdrawing anion used to treat the solid oxide is fluoride, chloride, bromide, iodide, phosphate, triflate, bisulfate, sulfate, fluoroborate, fluorosulfate, trifluoroacetate, phosphate, fluorophosphate, fluorozirconate, fluorosilicate, fluorotitanate, permanganate, substituted or unsubstituted alkanesulfonate, substituted or unsubstituted arenesulfonate, substituted or unsubstituted alkylsulfate, or any combination thereof.

16. A process for manufacturing a product comprising a polyolefin, the process comprising the acts of:
manufacturing a product at least a portion of which comprises a polyolefin, wherein the polyolefin is produced by a method comprising the act of:
contacting an α-olefin with a catalyst composition under polymerization conditions to form a polymer;
wherein the catalyst composition comprises the contact product of an ansa-metallocene and an activator, wherein:
the ansa-metallocene comprises a compound having the formula:

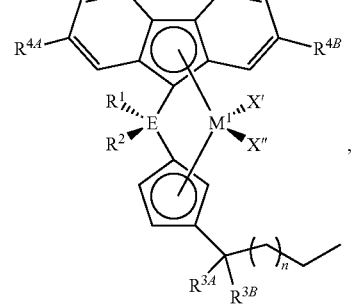

wherein:
M¹ is zirconium or hafnium;
X' and X" are independently F, Cl, Br, or I;
E is C or Si;
R¹ and R² are independently an alkyl group, an aryl group, or hydrogen;
R$^{3A}$ and R$^{3B}$ are independently a hydrocarbyl group, a trihydrocarbylsilyl group, or hydrogen;
n is an integer from 0 to 10, inclusive;
R$^{4A}$ and R$^{4B}$ are independently a hydrocarbyl group; and
the activator comprises an activator-support comprising a solid oxide treated with an electron-withdrawing anion; and
forming the polyolefin into the product.

17. The process of claim 16, wherein the activator comprises an organoaluminum compound having the formula:

Al(X$^5$)$_n$(X$^6$)$_{3-n}$, wherein:

X$^5$ is a hydrocarbyl;
X$^6$ is a halide, a hydride, an alkoxide or an aryloxide; and
n is a number from 1 to 3, inclusive.

18. The process of claim 16, wherein forming the product comprises at least one of extrusion, blow molding, injection molding, rotational molding, sheet extrusion, thermoforming, film blowing, film casting, or profile extrusion.

19. The process of claim 16, wherein the α-olefin comprises a monomer, or a monomer and a comonomer, and wherein the monomer comprises ethylene, propylene, or any combination thereof.

20. The process of claim 19, wherein the comonomer comprises propylene, 1-butene, 1-pentene, 1-hexene, 1-heptene, 1-octene, or any combination thereof.

* * * * *